(12) United States Patent
Crews et al.

(10) Patent No.: US 11,020,488 B2
(45) Date of Patent: Jun. 1, 2021

(54) PYRROLOQUINOLIN COMPOUNDS AND METHODS OF USING SAME

(71) Applicants: The Regents of the University of California, Oakland, CA (US); Henry Ford Health System, Detroit, MI (US)

(72) Inventors: Phillip Crews, Santa Cruz, CA (US); Frederick A. Valeriote, Washington, MI (US); Sheng Lin, Beijing (CN); Erin P. McCauley, Santa Cruz, CA (US); Nicholas Lorig-Roach, Santa Cruz, CA (US); Karen Tenney, Santa Cruz, CA (US)

(73) Assignees: The Regents of the University of California, Oakland, CA (US); Henry Ford Health System, Detroit, MI (US)

( * ) Notice: Subject to any disclaimer, the term of this patent is extended or adjusted under 35 U.S.C. 154(b) by 0 days.

(21) Appl. No.: 16/493,690

(22) PCT Filed: Mar. 13, 2018

(86) PCT No.: PCT/US2018/022263
§ 371 (c)(1),
(2) Date: Sep. 12, 2019

(87) PCT Pub. No.: WO2018/170019
PCT Pub. Date: Sep. 20, 2018

(65) Prior Publication Data
US 2020/0129631 A1    Apr. 30, 2020

Related U.S. Application Data

(60) Provisional application No. 62/471,261, filed on Mar. 14, 2017.

(51) Int. Cl.
*A61K 31/437* (2006.01)
*A61K 47/68* (2017.01)
*A61P 35/00* (2006.01)
*C07D 471/06* (2006.01)

(52) U.S. Cl.
CPC ........ *A61K 47/6803* (2017.08); *A61K 31/437* (2013.01); *A61P 35/00* (2018.01); *C07D 471/06* (2013.01)

(58) Field of Classification Search
CPC .................................................. A61K 47/6803
USPC .......................................................... 546/84
See application file for complete search history.

(56) References Cited

U.S. PATENT DOCUMENTS 5,414,001 A * 5/1995 Ireland ................. C07D 471/06
                                                            514/287
2010/0144779 A1    6/2010 Velu et al.

OTHER PUBLICATIONS

Alonso, Mar.Drugs 2016, 14, 197, 1-12.*
Lin, Marine Drugs, 2017 15(4), 98, 1-18, p. 7, last paragraph (for 112-1).*
Venkatesh , J. Pharm. Sci. 89, 145-54 (2000) (p. 146, left column).*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Lin Mar. Drugs 2017, 15, 98, 118.*
Schmidt, Journal of Natural Products (1995), 58(12), 1861-7.*
Dorwald F. A. Side Reactions in Organic Synthesis, 2005, Wiley: VCH, Weinheim p. IX of Preface p. 1-15.*
Alonso et al. (2016) "Evaluation of the Antioxidant Activity of the Marine Pyrroloiminoquinone Makaluvamines" Marine Drugs, 14(11):197.

(Continued)

*Primary Examiner* — Nizal S Chandrakumar
(74) *Attorney, Agent, or Firm* — Brian E. Davy; Bozicevic, Field & Francis LLP

(57) ABSTRACT

Provided are pyrroloquinolin compounds of formula (1) or (II). In certain aspects, the pyrroloquinolin compounds are therapeutic, e.g., for treating a cell proliferative disorder. Also provided are conjugates that include the pyrroloquinolin compounds of the present disclosure. Compositions, e.g., pharmaceutical compositions, that include the pyrroloquinolin compounds and conjugates of the present disclosure are also provided. Further provided are therapeutic methods involving the administration of the pyrroloquinolin compounds, conjugates or compositions of the present disclosure. Kits that include the pyrroloquinolin compounds, conjugates or compositions are also provided.

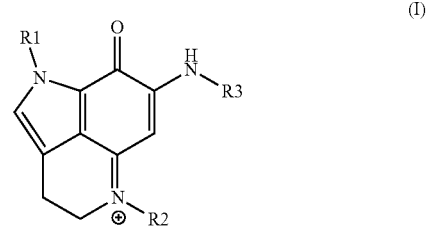

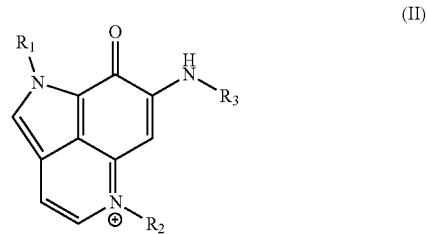

2 Claims, 16 Drawing Sheets

(56) References Cited

OTHER PUBLICATIONS

Dijoux et al. (2005) "Antitumor activity and distribution of pyrroloiminoquinones in the sponge genus *Zyzzya*" Bioorganic & Medicinal Chemistry, 13(21):6035-6044.

Ducry and Stump (2010) "Antibody-Drug Conjugates: Linking Cytotoxic Payloads to Monoclonal Antibodies" Bioconjugate Chem. 21:5-13.

Johnson et al. (2017) "Identification of the First Marine-Derived Opioid Receptor "Balanced" Agonist with a Signaling Profile That Resembles theEndorphins" ACS Chemical Neuroscience, 8(3):473-482.

Lin et al. (2017) "Another Look at Pyrroloiminoquinone Alkaloids-Perspectives on Their Therapeutic Potential from Known Structures and Semisynthetic Analogues" Marine Drugs, 15(4):98.

Wang et al. (2009) "In Vitro and In Vivo Anti-cancer Activity of Novel Synthetic Makaluvamine Analogs" Clin. Cancer Res., 15(10):3511-3518.

\* cited by examiner

FIG. 3

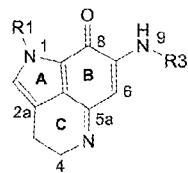
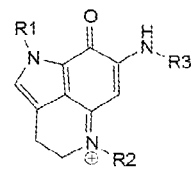

| Comp. | R1 | R3 |
|---|---|---|
| MAK A (1) | CH₃ | H |
| MAK D (7) | H | •CH₂CH₂-C₆H₄-OH |
| MAK K (10) | CH₃ | •CH₂CH₂-C₆H₄-OH |
| MAK A-Ac (13) | CH₃ | •C(O)CH₃ |

| Comp. | R1 | R2 | R3 |
|---|---|---|---|
| MAK C (2) | H | CH₃ | H |
| MAK H (4) | CH₃ | CH₃ | H |
| MAK G (8) | CH₃ | CH₃ | •CH=CH-C₆H₄-OH |
| MAK J (9) | H | CH₃ | •CH₂CH₂-C₆H₄-OH |
| MAK L (11) | H | CH₃ | •CH=CH-C₆H₄-OH |
| MAK P (12) | CH₃ | CH₃ | •CH₂CH₂-C₆H₄-OH |
| MAK J-Ac (15) | H | CH₃ | •CH₂CH₂-C₆H₄-OC(O)CH₃ |

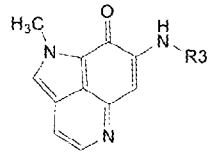

| Comp. | R1 | R3 |
|---|---|---|
| MAK B-Ac (14) | CH₃ | •C(O)CH₃ |

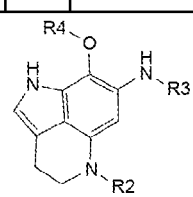

| Comp. | R2 | R3 | R4 |
|---|---|---|---|
| MAK J di-Ac (16) | CH₃ | •CH₂CH₂-C₆H₄-OC(O)CH₃ | •C(O)CH₃ |

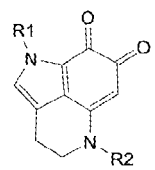

| Comp. | R1 | R2 |
|---|---|---|
| DAM A (5) | CH₃ | CH₃ |
| DAM B (3) | H | CH₃ |
| DAM D (6) | CH₃ | H |

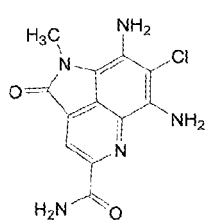

AMO B (17)

LEGEND
MAK = makaluvamine
DAM = damirone
AMO = ammosamide
Ac = acetate

FIG. 9
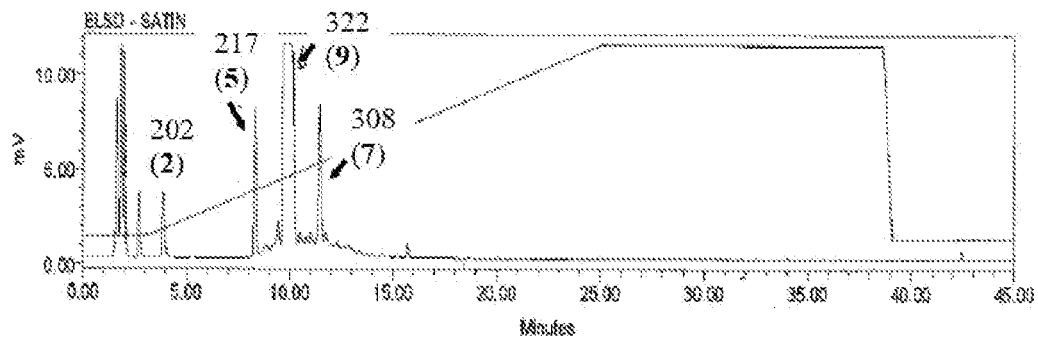
LC-ELSD chromatogram of 93132 DMM fraction
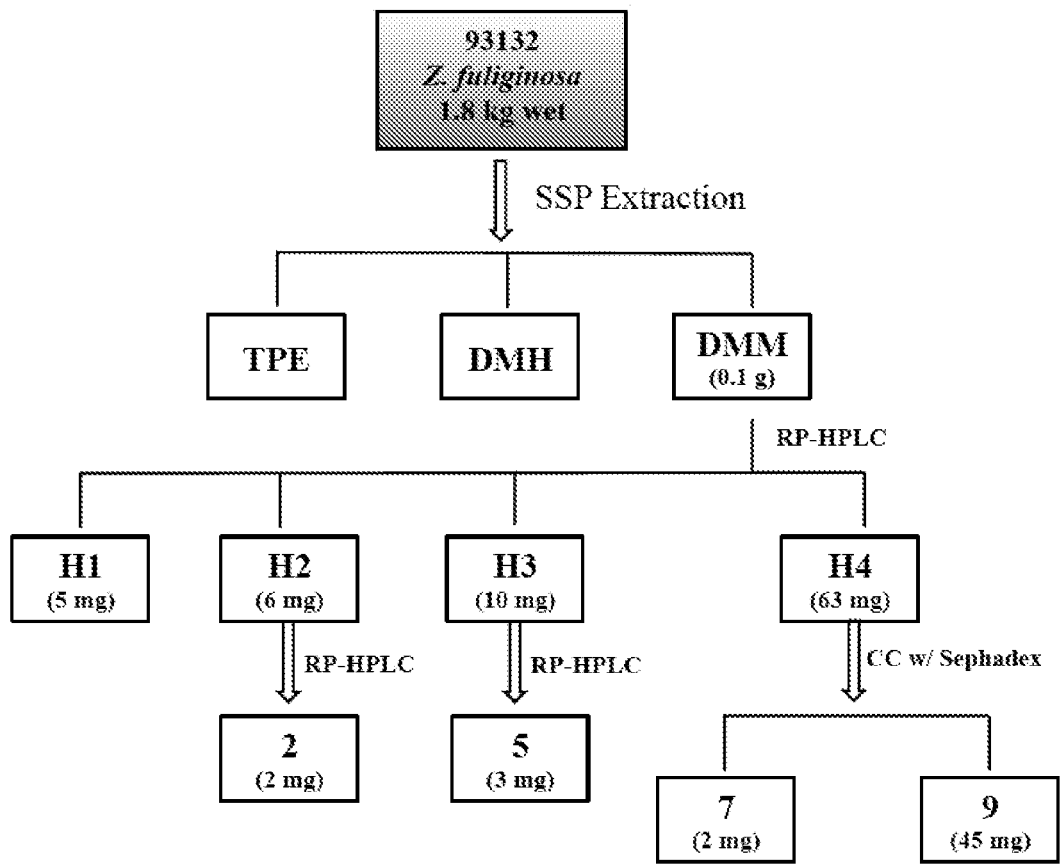

FIG. 10
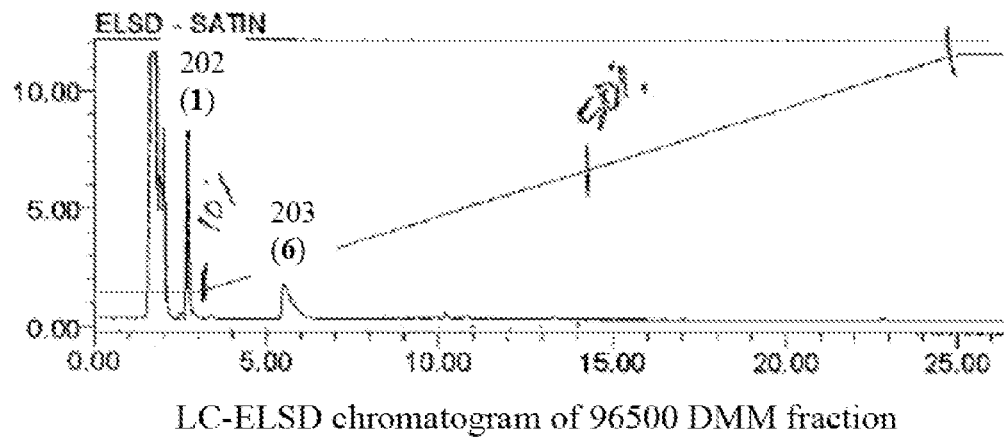
LC-ELSD chromatogram of 96500 DMM fraction
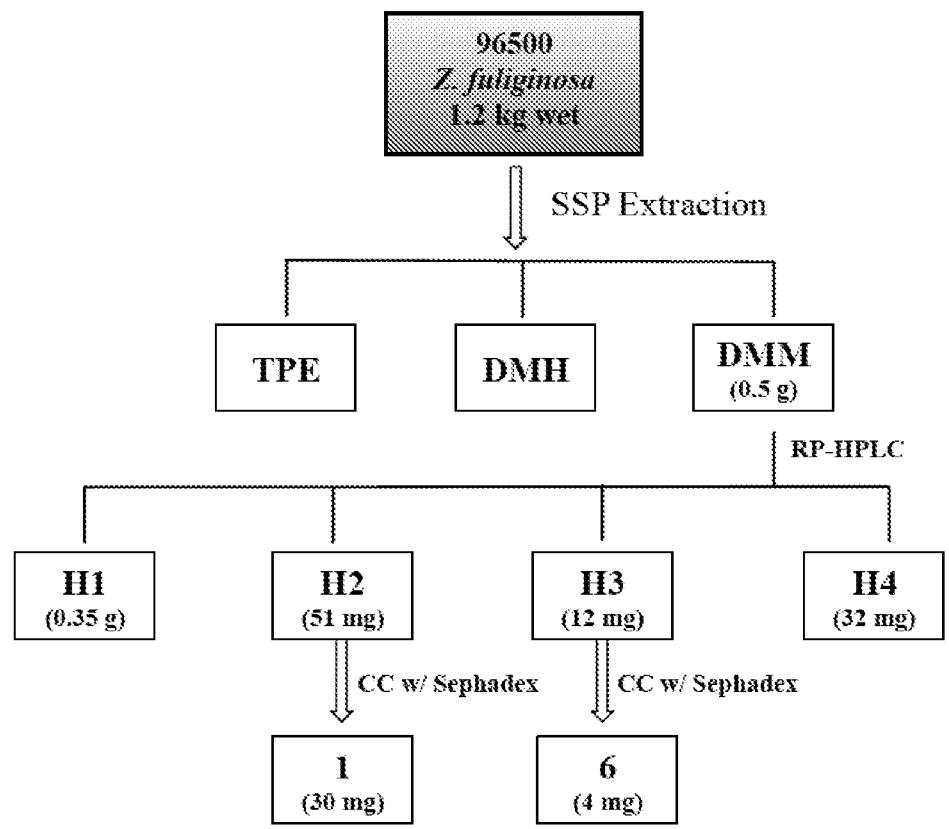

FIG. 11
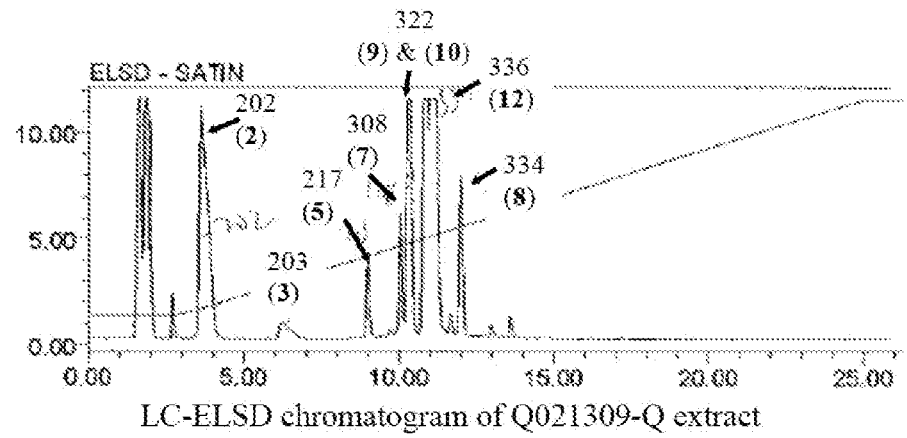
LC-ELSD chromatogram of Q021309-Q extract
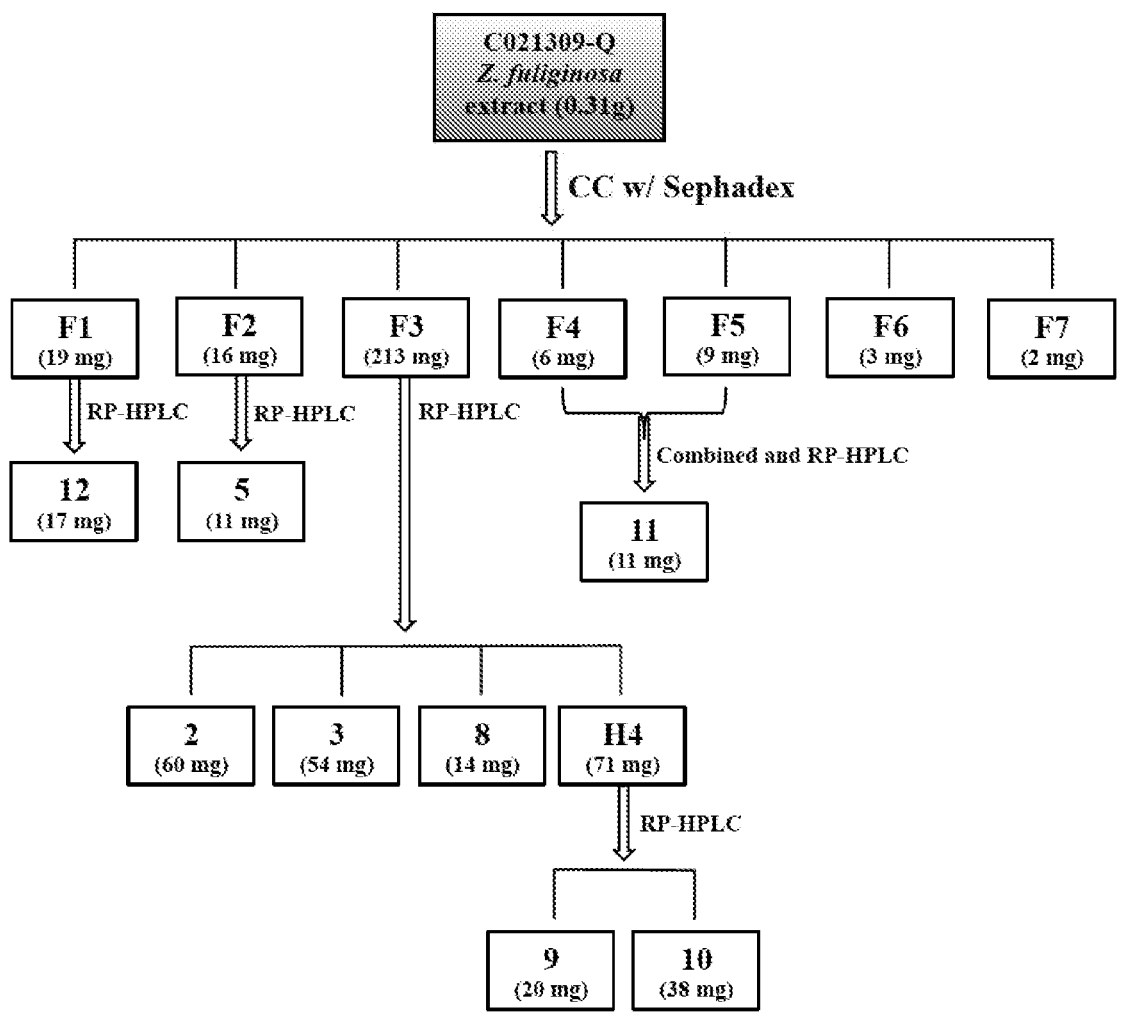

FIG. 12
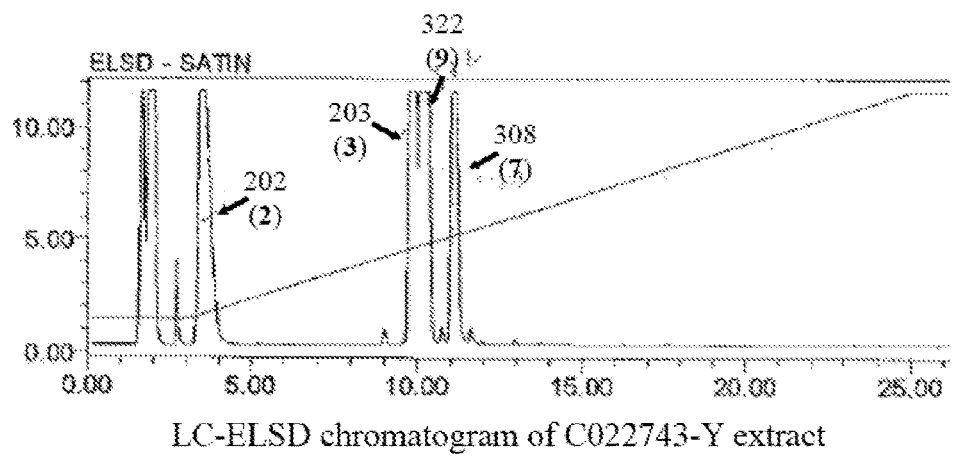
LC-ELSD chromatogram of C022743-Y extract
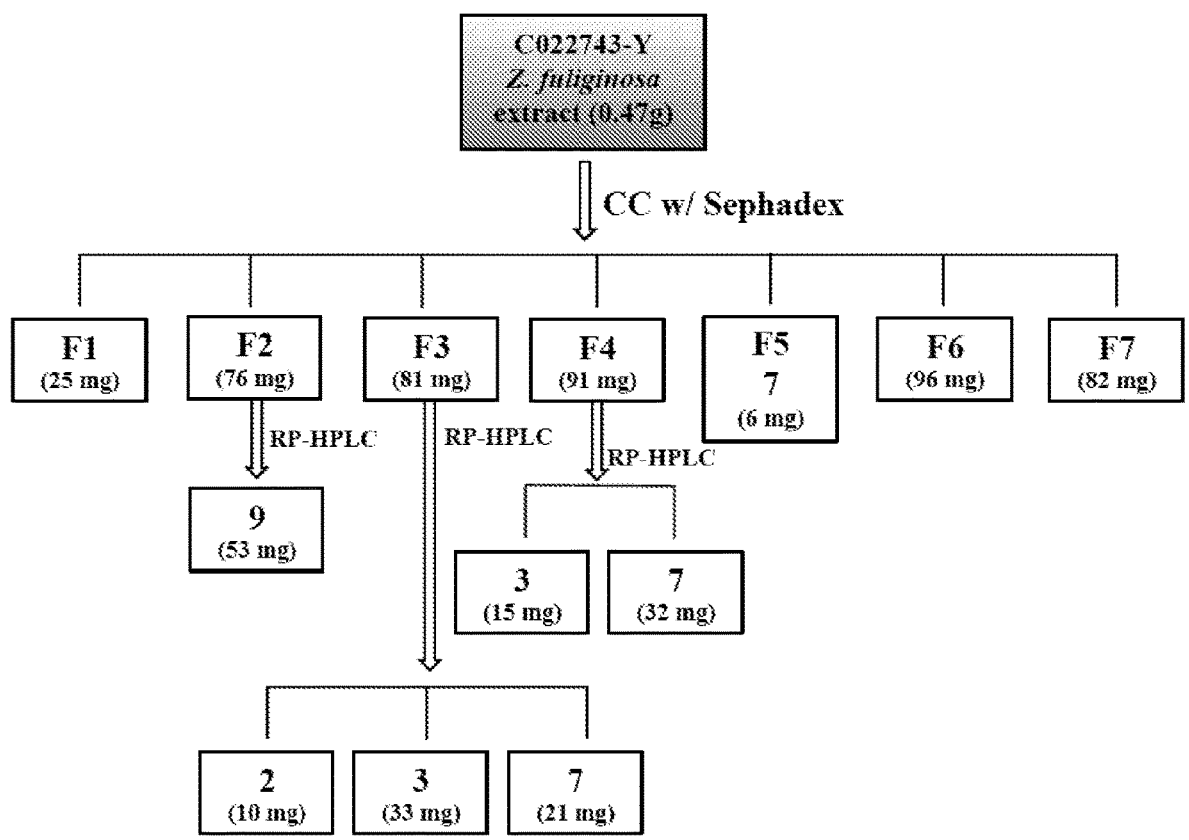

FIG. 13
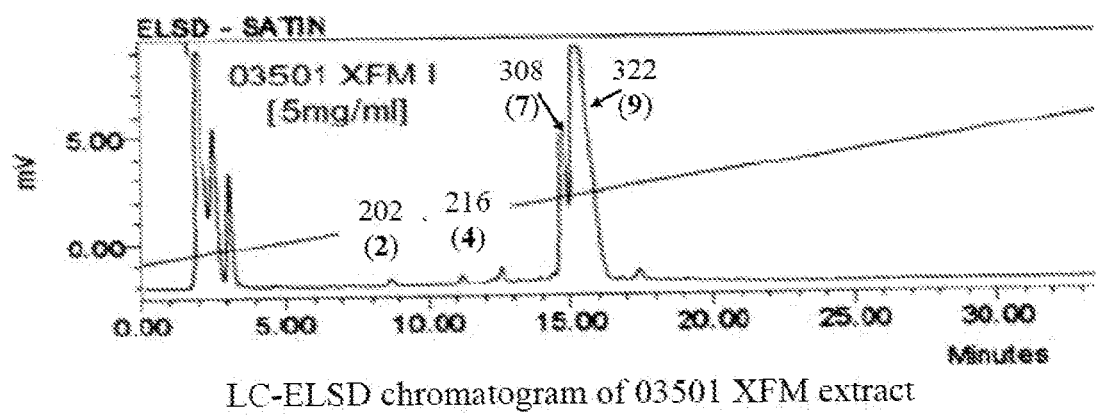
LC-ELSD chromatogram of 03501 XFM extract
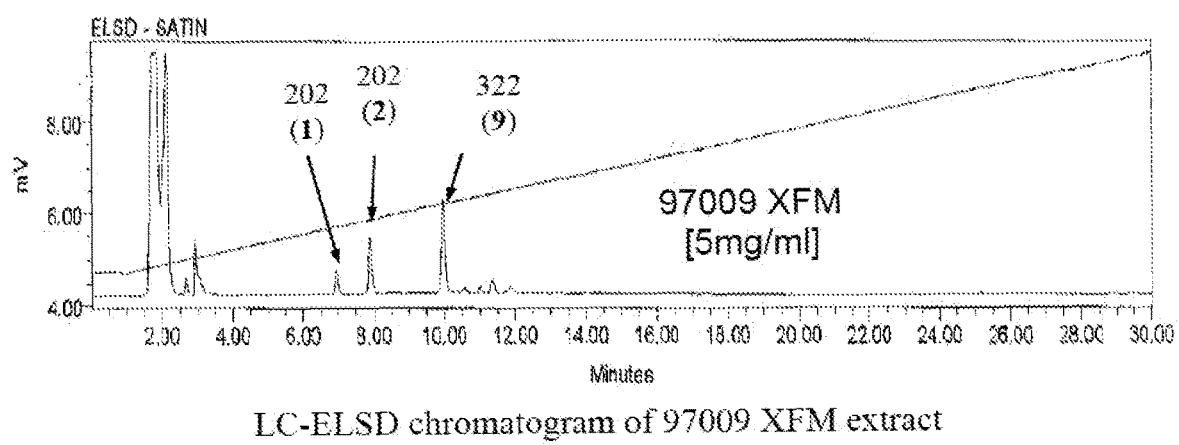
LC-ELSD chromatogram of 97009 XFM extract

FIG. 14
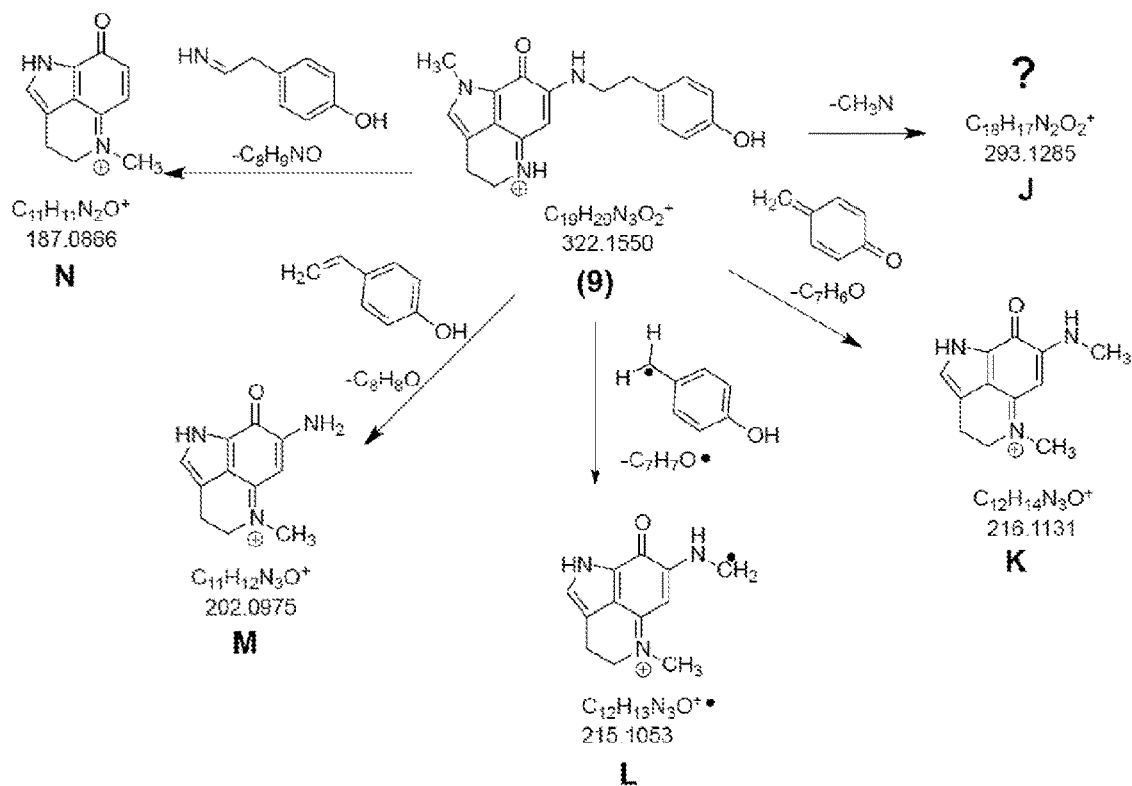
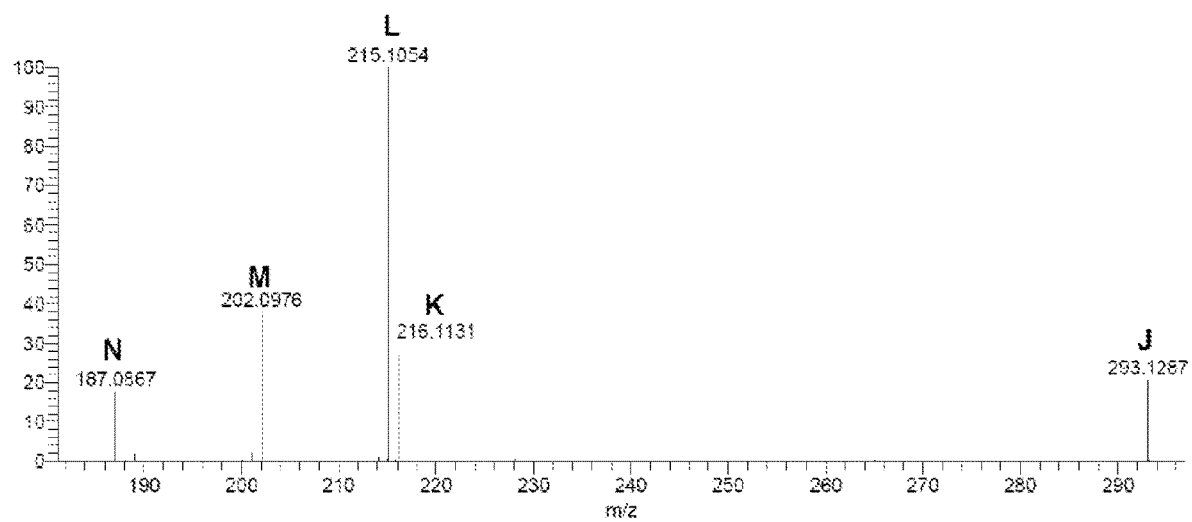

FIG. 15
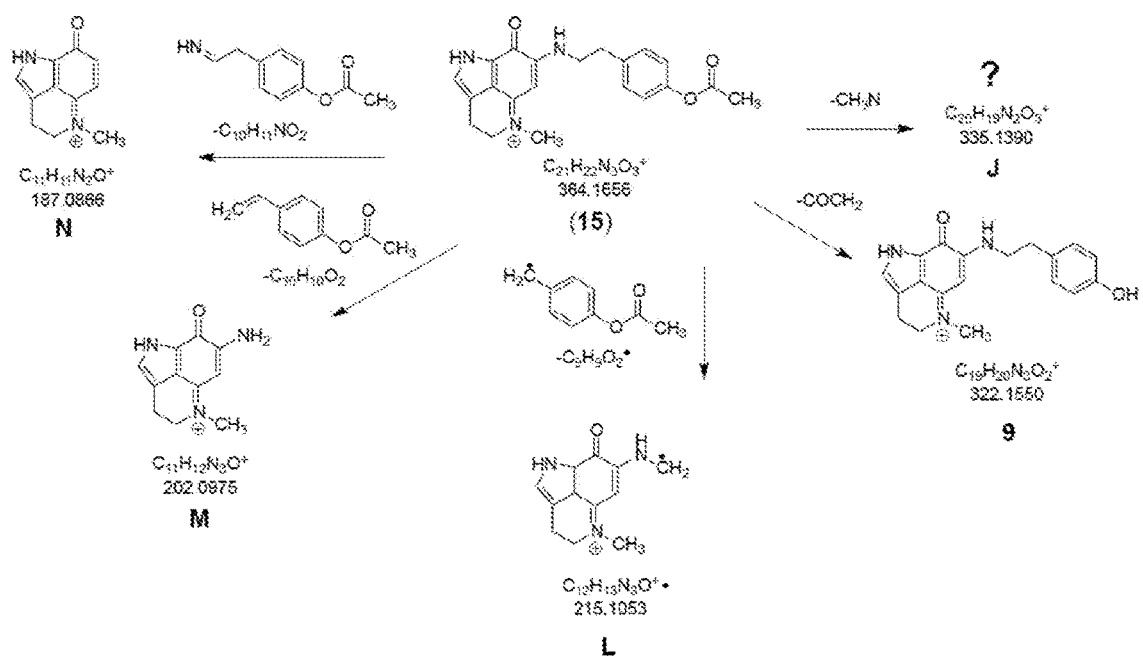
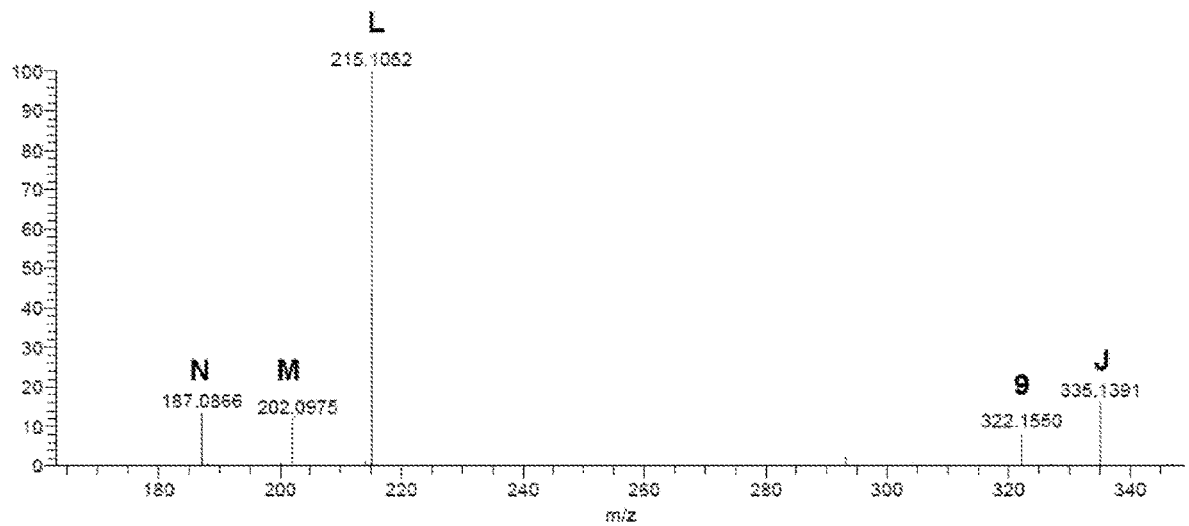

FIG. 16

| position | Mak A (1) | Mak C (2) | Dam B (3) | Mak H (4) | Dam A (5) | Dam D (6) | Mak D (7) | Mak G (8)[a] | Mak J (9) | Mak K (10) | Mak L (11)[a] | Mak P (12)[a] |
|---|---|---|---|---|---|---|---|---|---|---|---|---|
| 2 | 7.27, s | 7.27, s | 7.07, s | 7.30, s | 7.09, s | 7.09, s | 7.33, s | 7.09, s | 7.31, s | 7.17, s | 7.13, s | 7.08, s |
| 3 | 2.81, t (7.5) | 2.90, t (7.5) | 2.80, t (7.0) | 2.90, t | 2.77, t (7.0) | 2.69, t (7.0) | 2.87, t (7.5) | 2.98, t (7.5) | 2.92, t (7.5) | 2.77, t (7.5) | 3.02, t (7.5) | 2.94, t (7.5) |
| 4 | 3.77, t (7.5) | 3.84, t (7.5) | 3.59, t (7.0) | 3.90, m | 3.57, t (7.0) | 3.49, t (7.0) | 3.80, t (7.5) | 3.92, t (7.5) | 3.89, t (7.5) | 3.87, m | 3.96, t (7.5) | 3.87, t (7.5) |
| 6 | 5.61, s | 5.64, s | 5.11, s | 5.63, s | 5.12, s | 5.02, s | 5.50, s | 6.15, s | 5.59, s | 5.49, s | 6.16, s | 5.29, s |
| 10 | | | | | | | 3.45, t (7.5) | 7.48, d (14.5) | 3.60, t (7.0) | 3.33, brt (7.5) | 7.47, d (13.5) | 3.63, t (7.5) |
| 11 | | | | | | | 2.80, t (7.5) | 6.85, d (14.5) | 2.83, t (7.0) | 2.70, t (7.5) | 6.84, d (13.5) | 2.89, t (7.5) |
| 13 | | | | | | | 7.05, d (8.5) | 7.41, d (8.5) | 7.05, d (8.0) | 7.04, d (8.0) | 7.41, d (8.5) | 7.00, d (8.0) |
| 14 | | | | | | | 6.70, d (8.5) | 6.75, d (8.5) | 6.69, d (8.0) | 6.69, d (8.0) | 6.76, d (8.5) | 7.05, d (8.0) |
| N1-Me | 3.89, s | | | 3.84, s | 3.83, s | 3.83, s | | 3.96, s | | 3.87, s | | 3.93, s |
| N5-Me | | 3.27, s | 3.03, s | 3.33, s | 3.02, s | | | 3.48, s | 3.37, s | | 3.51, s | 3.31, s |
| N9-H | | | | | | | 9.00, br | 7.74, d (8.6) | | | | |
| NH | | | | | | 6.97, d (8.7) | 10.63, br | | | | 7.8, d (8.8) | |
| Ar-OH | | | | | | | 9.29, s | 9.73, s | 9.31, s | | | |

[a] $^1$H NMR was measured in CD$_3$OD

PYRROLOQUINOLIN COMPOUNDS AND METHODS OF USING SAME

CROSS-REFERENCE TO RELATED APPLICATIONS

This application claims the benefit of U.S. Provisional Patent Application No. 62/471,261, filed Mar. 14, 2017, which application is incorporated herein by reference in its entirety.

STATEMENT REGARDING FEDERALLY SPONSORED RESEARCH

This invention was made with Government support under contract number CA047135, awarded by the National Institutes of Health. The Government has certain rights in the invention.

INTRODUCTION

*Zyzzya fuliginosa*, a ubiquitous, black burrowing sponge exudes black mucus on collection. *Z. fuliginosa* reliably affords compounds possessing a pyrrolo[4,3,2-de]quinoline core. This framework is now considered to be created by a RiPP pathway delivering a C-terminal tryptophan building block.

Two sponge genera, *Zyzzya* and *Latrunculia*, are abundant sources of pyrrolo[4,3,2-de]quinolines, which now number close to 100 structures. To date only one compound, wakayin, has been isolated from a tunicate. Certain of such compounds are products of biosynthetic machinery present in microorganisms. Most notably, makaluvamine A repeatedly isolated from *Zyzzya* has also been reported from a terrestrial slime mold, and mushrooms produce further functionalized core skeletons represented by sanguinone A and mycenarubin A. Marine-derived Gram-positive microorganisms are the source of: (a) ammosamides possessing halogen substituents, and (b) lymphostins containing additional residues created by PKS biosynthesis. While several of the compounds inhibit druggable cancer targets, few of them exhibit single or double digit nanomolar in vitro potency.

SUMMARY

Provided are pyrroloquinolin compounds. In certain aspects, the pyrroloquinolin compounds are therapeutic, e.g., for treating a cell proliferative disorder. Also provided are conjugates that include the pyrroloquinolin compounds of the present disclosure. Compositions, e.g., pharmaceutical compositions, that include the pyrroloquinolin compounds and conjugates of the present disclosure are also provided. Further provided are therapeutic methods involving the administration of the pyrroloquinolin compounds, conjugates or compositions of the present disclosure. Kits that include the pyrroloquinolin compounds, conjugates or compositions are also provided.

BRIEF DESCRIPTION OF THE FIGURES

FIG. 3 Pyrrolo[4,3,2-de]quinoline-containing natural products screened against the PANC-1 cell line in this study consisting of: (i) makaluvamines A (1), C (2), H (4), D (7), G (8), J-L (9-11), P (12); (ii) damirones A (5), B (3), D (6); (iii) semisynthetic makaluvamine acetates 9-N-acetyl makaluvamine A (13), 9-N-acetyl makaluvamine B (14), 15-O-acetyl makaluvamine J (15), 8,15-O-diacetyl-8-hydroxy-5a, 7,8a-trien-makaluvamine J (16); and (iv) ammosamide B (17).

FIG. 9 Isolation scheme for compounds 2, 5, 7, and 9 from *Z. fuliginosa* 93132.

FIG. 10 Isolation scheme for compounds 1 and 6 from *Z. fuliginosa* 96500.

FIG. 11 Isolation scheme for compounds 2, 3, 5, and 8-12 from *Z. fuliginosa* C021309-Q.

FIG. 12 Isolation scheme for compounds 2, 3, 7, and 9 from *Z. fuliginosa* C022743-Y.

FIG. 13 LC-ELSD chromatograms showing compounds 2, 4, 7, and 9 from *Z. fuliginosa* 03501, and 1, 2, and 9 from *Z. fuliginosa* 97009.

FIG. 14 $MS^2$ spectrum and predicted fragmentation structures of makaluvamine J (9).

FIG. 15 $MS^2$ spectrum and predicted fragmentation structures of 15-O-acetyl makaluvamine J (15).

FIG. 16 $^1$H NMR data (500/600 MHz) for the makaluvamines (1, 2, 4, 7-12) and damirones (3, 5, 6) in DMSO-$d_6$.

DETAILED DESCRIPTION

Figure 1:
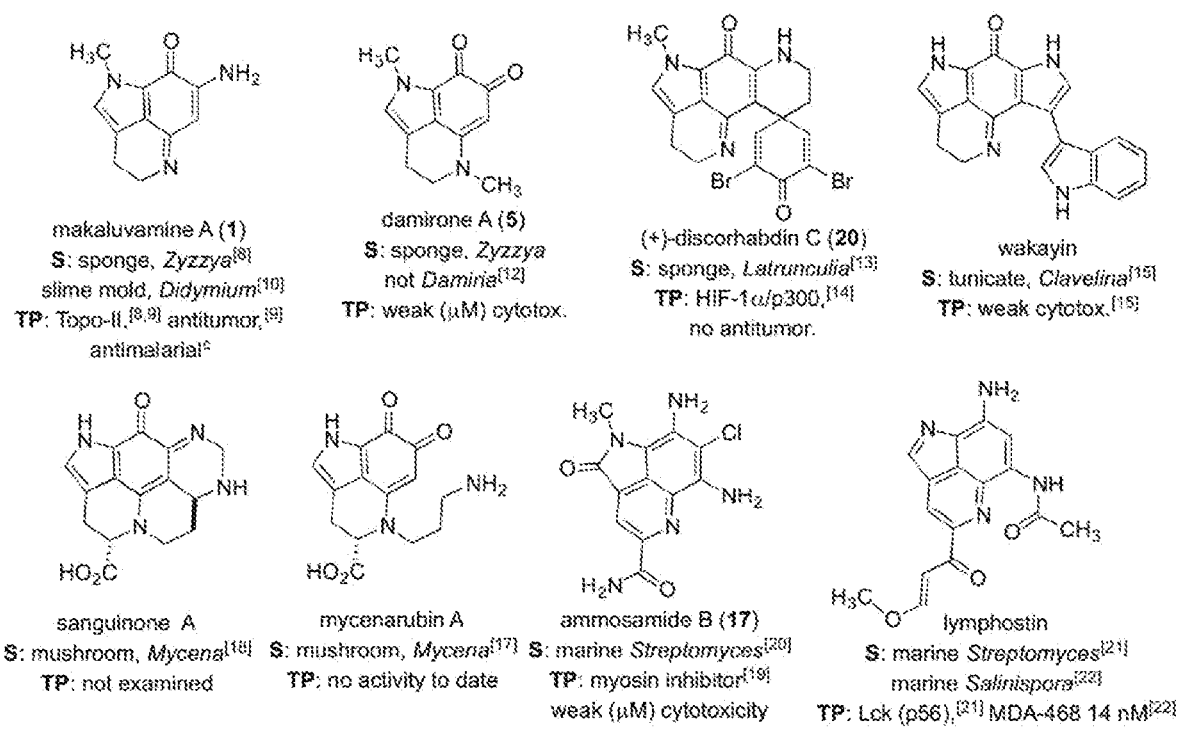
FIG. 1 provides a summary of natural products containing the $C_{10}N_2$ pyrrolo[4,3,2-de]quinoline core along with their sources (S) and therapeutic potential (TP).

Provided are pyrroloquinolin compounds. In certain aspects, the pyrroloquinolin compounds are therapeutic, e.g., for treating a cell proliferative disorder. Also provided are conjugates that include the pyrroloquinolin compounds of the present disclosure. Compositions, e.g., pharmaceutical compositions, that include the pyrroloquinolin compounds and conjugates of the present disclosure are also provided. Further provided are therapeutic methods involving the administration of the pyrroloquinolin compounds, conjugates or compositions of the present disclosure. Kits that include the pyrroloquinolin compounds, conjugates or compositions are also provided.

Before the compounds, conjugates, compositions, methods and kits of the present disclosure are described in greater detail, it is to be understood that the compounds, conjugates, compositions, methods and kits are not limited to particular embodiments described, as such may, of course, vary. It is also to be understood that the terminology used herein is for the purpose of describing particular embodiments only, and is not intended to be limiting, since the scope of the compounds, conjugates, compositions, methods and kits will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the compounds, conjugates, compositions, methods and kits. The upper and lower limits of these smaller ranges may independently be included in the smaller ranges and are also encompassed within the compounds, conjugates, compositions, methods and kits, subject to any specifically excluded limit in the stated range. Where the stated range includes one or both of the limits, ranges excluding either or both of those included limits are also included in the compounds, conjugates, compositions, methods and kits.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the compounds, conjugates, compositions, methods and kits belong. Although any compounds, conjugates, compositions, methods and kits similar or equivalent to those described herein can also be used in the practice or testing of the compounds, conjugates, compositions, methods and kits, representative illustrative compounds, conjugates, compositions, methods and kits are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present compounds, conjugates, compositions, methods and kits are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the compounds, conjugates, compositions, methods and kits, which are, for clarity, described in the context of separate embodiments, may also be provided in combination in a single embodiment. Conversely, various features of the compounds, conjugates, compositions, methods and kits, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present compounds, conjugates, compositions, methods and kits and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present compounds, conjugates, compositions, methods and kits. Any recited method can be carried out in the order of events recited or in any other order that is logically possible.

Definitions

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

The term "substituted alkyl" refers to an alkyl group as defined herein where one or more carbon atoms in the alkyl chain have been optionally replaced with a heteroatom such as —O—, —N—, —S—, (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, where R' and R" may be the same or different and are chosen from hydrogen, optionally substituted alkyl, cycloalkyl, alkenyl, cycloalkenyl, alkynyl, aryl, heteroaryl and heterocyclic.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Alkyl-aryl" refers to a group having both an alkyl group and an aryl group, which alkyl and aryl groups are defined above. "Substituted alkyl-aryl" refers to an alkyl-aryl group having one or more substitutions, including but not limited to, any of the substitutions described herein with respect to "substituted alkyl" and "substituted aryl" groups.

"Amino" refers to the group —NH$_2$.

"Carboxyl," "carboxy" or "carboxylate" refers to —CO$_2$H or salts thereof.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those where the compound is protonated by an inorganic or organic acid to form a cation, with the conjugate base of the inorganic or organic acid as the anionic component of the salt.

Compounds

As summarized above, aspects of the present disclosure include pyrroloquinolin compounds, e.g., therapeutic pyrroloquinolins. The compounds herein may be isolated from an organism. In certain aspects, the organism is a marine sponge, e.g., from a *Zyzzya fuliginosa* extract. As used herein, the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified. As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

In some embodiments, a pyrroloquinolin compound of the present disclosure is synthetic.

In certain aspects, a compound of the present disclosure has a pyrrolo[4,3,2-de]quinolin-7-amine core scaffold as shown below:

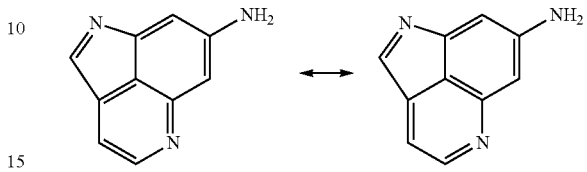

In some embodiments, provided is a compound as set forth in formula (I) or formula (II):

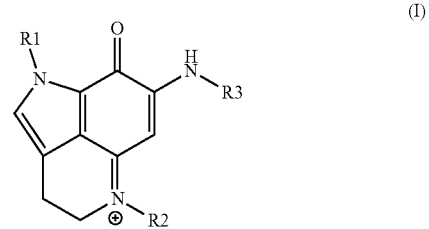

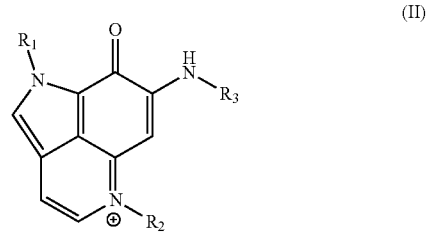

where $R^1$ is H, methyl, alkyl, substituted alkyl, alkyl-aryl, or substituted alkyl-aryl;

$R^2$ is methyl, alkyl, substituted alkyl, alkyl-aryl, or substituted alkyl-aryl; and $R^3$ is H, methyl, alkyl, substituted alkyl, alkyl-aryl, or substituted alkyl-aryl.

In certain aspects, the compound is that of formula (I). In other aspects, the compound is that of formula (II).

According to certain embodiments, when the compound is as set forth in formula (I) or formula (II), $R^1$ is H.

In some embodiments, when the compound is as set forth in formula (I) or formula (II), $R^2$ is methyl.

In certain aspects, when the compound is as set forth in formula (I) or formula (II), $R^3$ is substituted alkyl-aryl. According to certain embodiments, when the compound is as set forth in formula (I) or formula (II), $R^3$ is

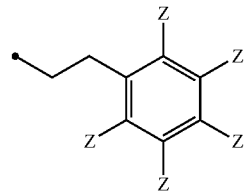

where each Z is independently selected from the group consisting of: H, —OH or —OAc, where at least one Z is —OH or —OAc. In certain aspects, for such a compound, R³ is

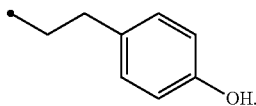

In some embodiments, for such a compound, each Z is independently selected from the group consisting of: H or —OAc. For example, in certain aspects, each Z is independently selected from the group consisting of: H or —OAc, where R3 includes at least one —OAc. In one non-limiting example, R³ is

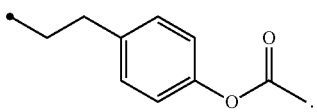

According to some embodiments, for a compound of formula (I) or formula (II), R³ is one of:

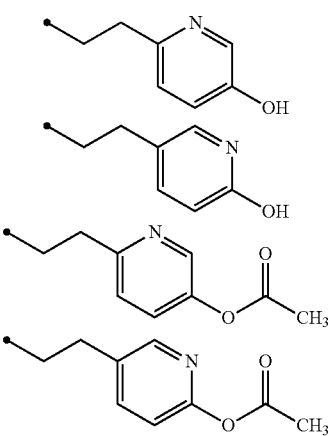

In certain aspects, provided is a compound as set forth in formula (III):

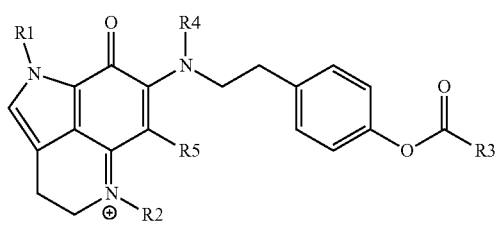

where

R¹ is H, methyl, alkyl, substituted alkyl, alkyl-aryl, or substituted alkyl-aryl;

R² is methyl, alkyl, substituted alkyl, alkyl-aryl, or substituted alkyl-aryl;

R³ is H, methyl, alkyl, substituted alkyl, alkyl-aryl, or substituted alkyl-aryl;

R⁴ is H, methyl, alkyl, substituted alkyl, alkyl-aryl, or substituted alkyl-aryl; and R⁵ is H, methyl, alkyl, substituted alkyl, alkyl-aryl, or substituted alkyl-aryl.

In some embodiments, provided is a compound as set forth in formula (IV):

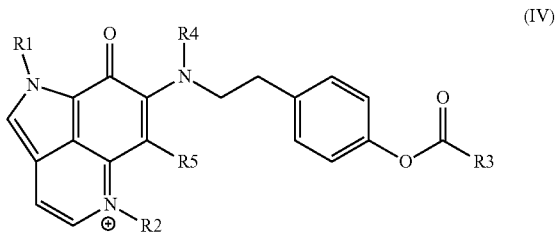

where

R¹ is H, methyl, alkyl, substituted alkyl, alkyl-aryl, or substituted alkyl-aryl;

R² is methyl, alkyl, substituted alkyl, alkyl-aryl, or substituted alkyl-aryl;

R³ is H, methyl, alkyl, substituted alkyl, alkyl-aryl, or substituted alkyl-aryl;

R⁴ is H, methyl, alkyl, substituted alkyl, alkyl-aryl, or substituted alkyl-aryl; and R⁵ is H, methyl, alkyl, substituted alkyl, alkyl-aryl, or substituted alkyl-aryl.

In certain aspects, provided is a compound as set forth in formula (V):

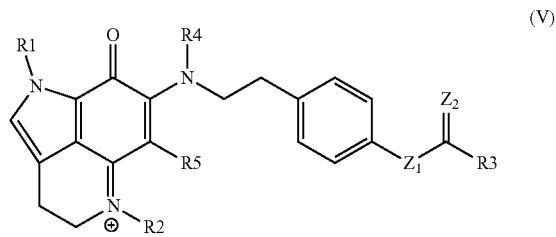

where

R¹ is H, methyl, alkyl, substituted alkyl, alkyl-aryl, or substituted alkyl-aryl;

R² is methyl, alkyl, substituted alkyl, alkyl-aryl, or substituted alkyl-aryl;

R³ is H, methyl, alkyl, substituted alkyl, alkyl-aryl, or substituted alkyl-aryl;

R⁴ is H, methyl, alkyl, substituted alkyl, alkyl-aryl, or substituted alkyl-aryl;

R⁵ is H, methyl, alkyl, substituted alkyl, alkyl-aryl, or substituted alkyl-aryl;

Z¹ is O or N; and

Z² is O or N.

According to some embodiments, provided is a compound as set forth in formula (VI):

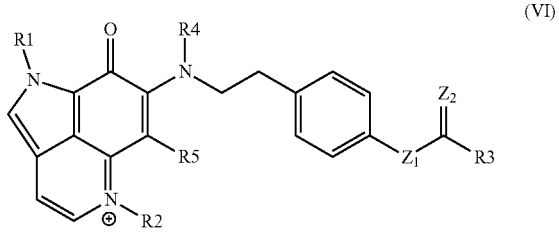

(VI)

where $R^1$ is H, methyl, alkyl, substituted alkyl, alkyl-aryl, or substituted alkyl-aryl;

$R^2$ is methyl, alkyl, substituted alkyl, alkyl-aryl, or substituted alkyl-aryl;

$R^3$ is H, methyl, alkyl, substituted alkyl, alkyl-aryl, or substituted alkyl-aryl;

$R^4$ is H, methyl, alkyl, substituted alkyl, alkyl-aryl, or substituted alkyl-aryl;

$R^5$ is H, methyl, alkyl, substituted alkyl, alkyl-aryl, or substituted alkyl-aryl;

$Z^1$ is O or N; and $Z^2$ is O or N.

In certain aspects, provided is a compound as set forth in formula (VII):

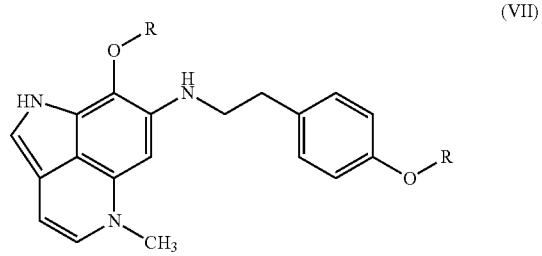

(VII)

where $R^1$ is H, methyl, alkyl, substituted alkyl, alkyl-aryl, or substituted alkyl-aryl; and $R^2$ is methyl, alkyl, substituted alkyl, alkyl-aryl, or substituted alkyl-aryl.

Compounds as set forth in formula (VII) do not have nano-molar cytotoxicity against PANC-1 and/or OVCAR tumor cells and, in some embodiments, find use alongside compounds such as those of formulas (I)-(VI) as a tool in target-finding experiments to launch pre-clinical research. Some of these compounds can be prepared by semi-synthesis from makaluvamine J.

In some embodiments, a compound of the present disclosure has a pyrrolo[4,3,2-de]quinoline core, and includes one, two, or all three of the following structural motifs: (1) conjugation within the core of the ABC-ring; (2) the presence of a positive charge in the C-ring; and/or (3) inclusion of a 4-ethyl phenol or 4-ethyl phenol acetate substituent off the B-ring.

Conjugates

Also provided are conjugates. The conjugates include a targeting moiety and any of the compounds described elsewhere herein. The targeting moiety and the compound are conjugated to one another. In certain aspects, such conjugates find use in therapeutic methods, e.g., to treat a cell proliferative disorder (e.g., cancer). In certain aspects, the compound of the conjugate has a pyrrolo[4,3,2-de]quinoline core, and includes one, two, or all three of the following structural motifs: (1) conjugation within the core of the ABC-ring; (2) the presence of a positive charge in the C-ring; and/or (3) inclusion of a 4-ethyl phenol or 4-ethyl phenol acetate substituent off the B-ring.

Any suitable targeting moiety may be employed. Targeting moieties of interest include, but are not limited to, a polypeptide (e.g., an antibody), a peptide, a ligand, a polynucleotide, an oligonucleotide, a small molecule, or the like.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant bacterial host cell); immunologically tagged proteins; and the like.

In certain aspects, the targeting moiety is an antibody. The term "antibody" includes monoclonal antibodies (including full length monoclonal antibodies), polyclonal antibodies, and multispecific antibodies (e.g., bispecific antibodies), humanized antibodies, single-chain antibodies (e.g., an scFv), chimeric antibodies, antibody fragments (e.g., Fab fragments), and the like. An antibody is capable of binding a target antigen. (Janeway, C., Travers, P., Walport, M., Shlomchik (2001) Immuno Biology, 5th Ed., Garland Publishing, New York). A target antigen can have one or more binding sites, also called epitopes, recognized by complementarity determining regions (CDRs) formed by one or more variable regions of an antibody.

According to some embodiments, the targeting moiety specifically binds to a target cell of interest. According to certain embodiments, the targeting moiety exhibits a binding affinity to a cell surface molecule of the target cell of a $K_d$ of less than or equal to about $10^{-5}$ M, less than or equal to about $10^{-6}$ M, or less than or equal to about $10^{-7}$ M, or less than or equal to about $10^{-8}$ M, or less than or equal to about $10^{-9}$ M, $10^{-10}$ M, $10^{-11}$ M, or $10^{-12}$ M or less. Such affinities may be readily determined using conventional techniques, such as by equilibrium dialysis, surface plasmon resonance (SPR) technology (e.g., the BIAcore 2000 instrument, using general procedures outlined by the manufacturer), radioimmunoassay, or by another method.

Target cells of interest include target cells responsible for a disease or disorder (e.g., a cell proliferative disorder) in an individual. For example, the target cell may be a cancer cell. By "cancer cell" is meant a cell exhibiting a neoplastic cellular phenotype, which may be characterized by one or more of, for example, abnormal cell growth, abnormal cellular proliferation, loss of density-dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell", "malignant cell" or "cancerous cell," and encompasses cancer cells of a solid tumor, a semi-solid tumor, a primary tumor, a metastatic tumor, and the like.

In certain aspects, the targeting moiety specifically binds to a cancer known to have one or more tumor-associated or tumor-specific cell surface molecules (e.g., cell surface receptors, membrane proteases, and the like) and the targeting moiety (e.g., an antibody) binds to an extracellular domain of one or more such tumor-associated or tumor-specific cell surface molecules. By "tumor-associated cell surface molecule" is meant a cell surface molecule expressed on malignant cells with limited expression on cells of normal tissues, a cell surface molecule expressed at much higher density on malignant versus normal cells, or a cell surface molecule that is developmentally expressed.

Any tumor-associated cell surface molecule or tumor-specific cell surface molecule may be targeted by a conjugate of the present disclosure. In certain aspects, the target on the cancer cell surface to which the targeting moiety (e.g., antibody) binds is HER2, CD19, CD22, CD30, CD33, CD56, CD66/CEACAM5, CD70, CD74, CD79b, CD138, Nectin-4, Mesothelin, Transmembrane glycoprotein NMB (GPNMB), Prostate-Specific Membrane Antigen (PSMA), SLC44A4, CA6, CA-IX, an integrin, C—X—C chemokine receptor type 4 (CXCR4), cytotoxic T-lymphocyte-associated protein 4 (CTLA-4), neuropilin-1 (NRP1), matriptase, or any other tumor-associated or tumor-specific cell surface molecules of interest.

In some embodiments, the targeting moiety and the compound are directly conjugated to each other. In other embodiments, the targeting moiety and the compound are conjugated to each other via a linker. Linkers that find use in the conjugates of the present disclosure include ester linkers, amide linkers, maleimide or maleimide-based linkers; valine-citrulline linkers; hydrazone linkers; N-succinimidyl-4-(2-pyridyldithio)butyrate (SPDB) linkers; Succinimidyl-4-(N-maleimidomethyl)cyclohexane-1-carboxylate (SMCC) linkers; vinylsulfone-based linkers; linkers that include polyethylene glycol (PEG), such as, but not limited to tetraethylene glycol; linkers that include propanoic acid; linkers that include caproleic acid, and linkers including any combination thereof.

In certain aspects, the linker is a chemically-labile linker, such as an acid-cleavable linker that is stable at neutral pH (bloodstream pH 7.3-7.5) but undergoes hydrolysis upon internalization into the mildly acidic endosomes (pH 5.0-6.5) and lysosomes (pH 4.5-5.0) of a target cell (e.g., a cancer cell). Chemically-labile linkers include, but are not limited to, hydrazone-based linkers, oxime-based linkers, carbonate-based linkers, ester-based linkers, etc. According to certain embodiments, the linker is an enzyme-labile linker, such as an enzyme-labile linker that is stable in the bloodstream but undergoes enzymatic cleavage upon internalization into a target cell, e.g., by a lysosomal protease (such as cathepsin or plasmin) in a lysosome of the target cell (e.g., a cancer cell). Enzyme-labile linkers include, but are not limited to, linkers that include peptidic bonds, e.g., dipeptide-based linkers such as valine-citrulline linkers, such as a maleimidocaproyl-valine-citruline-p-aminobenzyl (MC-vc-PAB) linker, a valyl-alanyl-para-aminobenzyloxy (Val-Ala-PAB) linker, and the like. Chemically-labile linkers, enzyme-labile, and non-cleavable linkers are known and described in detail, e.g., in Ducry & Stump (2010) *Bioconjugate Chem.* 21:5-13.

Numerous strategies are available for linking the compound to the targeting moiety (e.g., an antibody) through a linker. For example, a compound may be derivatized by covalently attaching the linker to the compound, where the linker has a functional group capable of reacting with a "chemical handle" on the targeting moiety. The functional group on the linker may vary and may be selected based on compatibility with the chemical handle on the targeting moiety. According to one embodiment, the chemical handle on the targeting moiety is provided by incorporation of an unnatural amino acid having the chemical handle into the targeting moiety. Such an unnatural amino acid may be incorporated via chemical synthesis or recombinant approaches, e.g., using a suitable orthogonal amino acyl tRNA synthetase-tRNA pair for incorporation of the unnatural amino acid during translation in a host cell.

It will be appreciated that the particular approach for attaching the linker to the compound and the linker to the targeting moiety will vary depending upon the particular compound and functional groups selected and employed in the linker and targeting moiety. According to certain embodiments, the conjugate includes (or is made from) makaluvamine J. In other embodiments, the conjugate includes (or is made from) makaluvamine J acetate.

Compositions

Also provided by the present disclosure are compositions. The compositions may include any of the compounds or conjugates described herein (e.g., a conjugate having any of the targeting moieties and compounds described herein). In some embodiments, provided are compositions (e.g., pharmaceutical or non-pharmaceutical compositions) including a compound or conjugate of the present disclosure, where the compound has a pyrrolo[4,3,2-de]quinoline core, and includes one, two, or all three of the following structural motifs: (1) conjugation within the core of the ABC-ring; (2) the presence of a positive charge in the C-ring; and/or (3) inclusion of a 4-ethyl phenol or 4-ethyl phenol acetate substituent off the B-ring.

In certain aspects, the compositions include a compound or conjugate of the present disclosure present in a liquid medium. The liquid medium may be an aqueous liquid medium, such as water, a buffered solution, or the like. One or more additives such as a salt (e.g., NaCl, $MgCl_2$, KCl, $MgSO_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS), N-tris[Hydroxymethyl] methyl-3-aminopropanesulfonic acid (TAPS), etc.), a solubilizing agent, a detergent (e.g., a non-ionic detergent such as Tween-20, etc.), a ribonuclease inhibitor, glycerol, a chelating agent, and the like may be present in such compositions.

Pharmaceutical compositions are also provided. The pharmaceutical compositions include any of the compounds or conjugates of the present disclosure, and a pharmaceutically acceptable carrier. The pharmaceutical compositions generally include a therapeutically effective amount of the compound or conjugate. By "therapeutically effective amount" is meant a dosage sufficient to produce a desired result, e.g., an amount sufficient to effect beneficial or desired therapeutic (including preventative) results, such as a reduction in a symptom of a disease or disorder (e.g., a cell proliferative disorder), as compared to a control. An effective amount can be administered in one or more administrations.

A compound or conjugate of the present disclosure can be incorporated into a variety of formulations for therapeutic administration. More particularly, the compound or conjugate can be formulated into pharmaceutical compositions by combination with appropriate, pharmaceutically acceptable excipients or diluents, and may be formulated into preparations in solid, semi-solid, liquid or gaseous forms, such as tablets, capsules, powders, granules, ointments, solutions, injections, inhalants and aerosols.

Formulations of the compounds or conjugates of the present disclosure suitable for administration to an individual (e.g., suitable for human administration) are generally sterile and may further be free of detectable pyrogens or other contaminants contraindicated for administration to a patient according to a selected route of administration.

In pharmaceutical dosage forms, the compounds or conjugates can be administered in the form of their pharmaceutically acceptable salts, or they may also be used alone or in appropriate association, as well as in combination, with other pharmaceutically active compounds. The following methods and carriers/excipients are merely examples and are in no way limiting.

For oral preparations, the compound or conjugate can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compound or conjugate can be formulated for parenteral (e.g., intravenous, intra-arterial, intraosseous, intramuscular, intracerebral, intracerebroventricular, intrathecal, subcutaneous, etc.) administration. In certain aspects, the compound or conjugate is formulated for injection by dissolving, suspending or emulsifying the compound or conjugate in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions that include the compound or conjugate may be prepared by mixing the compound or conjugate having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, where the lyophilized preparation is to be reconstituted with a sterile solution prior to administration. The standard procedure for reconstituting a lyophilized composition is to add back a volume of pure water (typically equivalent to the volume removed during lyophilization); however solutions including antibacterial agents may be used for the production of pharmaceutical compositions for parenteral administration.

An aqueous formulation of the compound or conjugate may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent may be included in the formulation to modulate the tonicity of the formulation. Example tonicity agents include sodium chloride, potassium chloride, glycerin and any component from the group of amino acids, sugars as well as combinations thereof. In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 mM.

A surfactant may also be added to the formulation to reduce aggregation and/or minimize the formation of particulates in the formulation and/or reduce adsorption. Example surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark Tween 20™) and polysorbate 80 (sold under the trademark Tween 80™). Examples of suitable polyethylene-polypropylene copolymers are those sold under the names Pluronic® F68 or Poloxamer 188™. Examples of suitable Polyoxyethylene alkyl ethers are those sold under the trademark Brij™. Example concentrations of surfactant may range from about 0.001% to about 1% w/v.

A lyoprotectant may also be added in order to protect the compound or conjugate against destabilizing conditions during a lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, the pharmaceutical composition includes a compound or conjugate of the present disclosure, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

Methods

As summarize above, the present disclosure provides methods. In certain aspects, a method of the present disclosure includes administering to an individual in need thereof a therapeutically effective amount of any of the compounds of the present disclosure, any of the conjugates of the present disclosure, or any of the pharmaceutical compositions of the present disclosure. In some embodiments, the compound has a pyrrolo[4,3,2-de]quinoline core, and includes one, two, or all three of the following structural motifs: (1) conjugation within the core of the ABC-ring; (2) the presence of a positive charge in the C-ring; and/or (3) inclusion of a 4-ethyl phenol or 4-ethyl phenol acetate substituent off the B-ring. In certain aspects, the individual in need thereof has a cell proliferative disorder, and the administering is effective in treating the cell proliferative disorder.

In some embodiments, the cell proliferative disorder is cancer. Cancers of interest include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, various types of head and neck cancer, and the like. In certain aspects, the cancer is pancreatic cancer. According to some embodiments, the cancer is ovarian cancer.

The compounds, conjugates or pharmaceutical compositions of the present disclosure are administered to the individual using any available method and route suitable for drug delivery, including in vivo and ex vivo methods, as well as systemic and localized routes of administration. Conventional and pharmaceutically acceptable routes of administration include intranasal, intramuscular, intra-tracheal, subcutaneous, intradermal, topical application, ocular, intravenous, intra-arterial, nasal, oral, and other enteral and parenteral routes of administration. Routes of administration may be combined, if desired, or adjusted depending upon the conjugate and/or the desired effect. The compound, conjugate or pharmaceutical composition may be administered in a single dose or in multiple doses. In some embodiments, the compound, conjugate or pharmaceutical composition is administered orally. In some embodiments, the compound, conjugate or pharmaceutical composition is administered via an inhalational route. In some embodiments, the compound, conjugate or pharmaceutical composition is administered intranasally. In some embodiments, the compound, conjugate or pharmaceutical composition is administered locally. In some embodiments, the compound, conjugate or pharmaceutical composition is administered ocularly. In some embodiments, the compound, conjugate or pharmaceutical composition is administered intracranially. In some embodiments, the compound, conjugate or pharmaceutical composition is administered parenterally (e.g., intravenously). In some embodiments, the conjugate is administered by injection, e.g., for systemic delivery (e.g., intravenous infusion) or to a local site.

A variety of individuals are treatable according to the subject methods. Generally such individuals are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the individual is a human.

By "treat," "treating" or "treatment" is meant at least an amelioration of the symptoms associated with the pathological condition afflicting the individual, where amelioration is used in a broad sense to refer to at least a reduction in the magnitude of a parameter, e.g., symptom, associated with the pathological condition being treated, such as disease or disorder associated with (e.g., caused by) a target cell or population thereof. As such, treatment also includes situations where the pathological condition, or at least symptoms associated therewith, are completely inhibited, e.g., prevented from happening, or stopped, e.g. terminated, such that the individual no longer suffers from the pathological condition, or at least the symptoms that characterize the pathological condition.

Dosing is dependent on severity and responsiveness of the disease state to be treated. Optimal dosing schedules can be calculated from measurements of compound or conjugate accumulation in the body of the individual. The administering physician can determine optimum dosages, dosing methodologies and repetition rates. Optimum dosages may vary depending on the relative potency of the compound or conjugate, and can generally be estimated based on $EC_{50}$s found to be effective in in vitro and in vivo animal models, etc. In general, dosage is from 0.01 µg to 100 g per kg of body weight, and may be given once or more daily, weekly, monthly or yearly. In some embodiments, the compound or conjugate is administered once. In some embodiments, the compound or conjugate is administered daily for a limited period of time (e.g., daily for 2 or more, 3 or more, 4 or more, 5 or more, 7 or more, 14 or more, or 21 or more days) or indefinitely. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, where the compound or conjugate is administered in maintenance doses, once or more daily, to once every several months, once every six months, once every year, or at any other suitable frequency.

The therapeutic methods of the present disclosure may include administering a single type of compound or conjugate to an individual, or may include administering two or more types of compounds or conjugates to an individual, e.g., a cocktail of different compounds and/or conjugates. In certain aspects, a compound or conjugate of the present disclosure is administered to the individual in combination with a second therapeutic agent (e.g., an anti-cancer agent). Such administration may include administering the compound or conjugate and the second agent concurrently, or administering the conjugate and the second agent sequentially.

Kits

As summarize above, the present disclosure provides kits. According to certain embodiments, the kits include any of the compounds, conjugates or compositions of the present disclosure. The kits find use, e.g., in practicing the methods of the present disclosure. For example, kits for practicing the subject methods may include a quantity of the compositions of the present disclosure, present in unit dosages, e.g., ampoules, or a multi-dosage format. As such, in certain embodiments, the kits may include one or more (e.g., two or more) unit dosages (e.g., ampoules) of a composition that includes a compound or conjugate of the present disclosure. The term "unit dosage", as used herein, refers to physically discrete units suitable as unitary dosages for human and animal subjects, each unit containing a predetermined quantity of the composition calculated in an amount sufficient to produce the desired effect. The amount of the unit dosage depends on various factors, such as the particular compound or conjugate employed, the effect to be achieved, and the pharmacodynamics associated with the compound or conjugate in the subject. In yet other embodiments, the kits may include a single multi dosage amount of the composition.

Components of the kits may be present in separate containers, or multiple components may be present in a single container. A suitable container includes a single tube (e.g., vial), one or more wells of a plate (e.g., a 96-well plate, a 384-well plate, etc.), or the like.

According to certain embodiments, a kit of the present disclosure includes instructions for using the compound, conjugate or composition to treat an individual in need thereof. In certain aspects, the individual in need thereof is an individual having a cell proliferative disorder, e.g., cancer. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

The following examples are offered by way of illustration and not by way of limitation.

EXPERIMENTAL

Introduction

A priority in the present study of marine-derived alkaloids has been to explore bioactive products isolable from both sponges and microorganisms. Exploring such molecules offers the prospect of rapidly assembling multi-compound libraries for comprehensive bioactivity and biosynthetic investigations. High profile, contemporary examples of such campaigns include studies from the inventors and from others involving bioactive entities such as: (i) bengamides from sponges (*Jaspis coriacea*) [1] and Gram-negative bacteria (*Myxococcus virescens*) [2,3] (ii) manzamines from sponges (*Acanthostrongylophora* sp.) [4] and Gram-positive bacteria (*Micromonospora* sp. strain M42), [5] and (iii) onnamide A from sponges (*Theonella swinhoei*, yellow chemotype) [6] and the sponge-associated *Candidatus entotheonella* [7]. Motivated by the potential to expand on this circumstance a deep examination of *Zyzzya* sponge metabolites was commenced to further assess their bioactivity and to design future experiments that probe the potential of this sponge as a source of chemically prolific bacteria.

During expeditions to multiple Indo-Pacific sites, attention was repeatedly drawn to *Zyzzya fuliginosa*, a ubiquitous, black burrowing sponge that exudes black mucus on collection. *Z. fuliginosa* reliably affords compounds possessing the pyrrolo[4,3,2-de]quinoline core shown in FIG. 1. Several specimens in the inventors' repository were flagged for a priority study when a methanol extract fraction of *Z. fuliginosa* (coll. no. 93132 DMM) obtained from Papua New Guinea exhibited potent and selective in vitro cytotoxic activity against the human pancreas/duct epithelioid carcinoma (PANC-1) cell line. Solvent partitioning of the crude extract concentrated the activity into a highly pigmented methanol fraction whose $^1$H NMR spectrum displayed low-field singlets at δ 7.3/δ 6.3 and upfield $A_2X_2$ multiplets δ 3.8/δ 2.9 characteristic of makaluvamines [8-15]. The paucity of pancreatic cancer selective agents useful as either therapeutic leads or clinical agents prompted exploratory work to isolate *Z. fuliginosa* constituents and then prepare new semi-synthetic analogs of the most active makaluvamines. A goal was to identify one or more potent (low nanomolar active) compounds active against pancreatic tumor cell lines.

At an early stage in the project, sought was understanding on the scope of natural "makaluvamine-type" scaffolds known from the marine and terrestrial environment. Highlights of important patterns shown in FIG. 1 are organized around compounds containing the $C_{10}N_2$ pyrrolo[4,3,2-de]quinoline. This framework is now considered to be created by a RiPP pathway delivering a C-terminal tryptophan building block [16]. The compilation in FIG. 1 also abstracts therapeutic assessment outcomes for eight different lead structures [8-15,17-22]. Two sponge genera, *Zyzzya* and *Latrunculia*, [23] are abundant sources of pyrrolo[4,3,2-de]quinolines, which now number close to 100 structures. To date only one compound, wakayin [15], has been isolated from a tunicate. Also, five of the molecules in FIG. 1 are products of biosynthetic machinery present in microorganisms. Most notably, makaluvamine A (1) repeatedly isolated from *Zyzzya* [23] has also been reported from a terrestrial slime mold [10], and mushrooms produce further functionalized core skeletons represented by sanguinone A [18] and mycenarubin A [17]. Marine-derived Gram-positive microorganisms are the source of: (a) ammosamides [19,20] possessing halogen substituents, and (b) lymphostins [21-22] containing additional residues created by PKS biosynthesis. While several of the compounds in FIG. 1 inhibit druggable cancer targets, few of them shown here or elsewhere exhibit single or double digit nanomolar in vitro potency.

Motivated by the positive PANC-1 selective data for the *Z. fuliginosa* (coll. no. 93132) extract, a searched for additional literature data was conducted. These surveys revealed four pyrrolo[4,3,2-de]quinolines: isobatzelline A, C, D, and secobatzelline A, from a Caribbean sponge *Batzella* sp. [23], and one synthetic analog, FBA-TPQ (7-(4-fluorobenzylamino)-1,3,4,8-tetrahydropyrrolo[4,3,2-de]quinolin-8(1H)-one) [25], which displayed moderate cytotoxicity against PANC-1 cells. Thus far, there have been no comprehensive studies on the makaluvamines evaluating their cytotoxicity against PANC-1 cells; but the pyrrolo[4,3,2-de]quinoline, isobatzellin C, a poor topoisomerase II inhibitor, exhibited an $IC_{50}$ of 10 μM against PANC-1 [26]. Described herein is the isolation, structure modification, and bioactivity assessment of nine makaluvamines, three damirones, and four new semisynthetic acetate esters. Once the structures of this collection were established, data against PANC-1 and OVCAR-5 cell lines was obtained to establish a structure-in vitro cytotoxicity activity relationship for this class of molecules.

The experimental design employed in this study involved the assembly of a small compound library consisting of natural and semi-synthetic pyrrolo[4,3,2-de]quinolines for additional study of their potential as leads for marine derived anti-cancer drugs. The major mechanism of action for this class has been described as involving topoisomerase II inhibition, which has dampened enthusiasm for their further study. The new twist here involved assembling a library of compounds for detailed evaluation as selective cytotoxins that could involve different molecular targets. Even though no new natural analogues were being pursued in the present study, it appeared productive to further explore bioassay properties of the pyrrolo[4,3,2-de]quinolines by further functionalizing the amino side chain with various substituents. Such structures are analogous to the family of TPQ synthetic analogs extensively explored by Velu and Zhang [27] whose properties relative to those of the makaluvamines will be further discussed below.

Example 1—Isolation of Pyrroloquinolin Compounds

The present study began with a focused re-investigation of *Zyzzya* sponges in order to isolate and re-screen makaluvamines C, H, and I described in 2005 [9] as "most potent and differential." Of further relevance is that two of these compounds exhibited promising in vivo T/C % (tumor volume in treated/tumor volume in untreated) in KB mouse model xenografts (H=38%, I=34%) [9]. Since that publication, none of these compounds or other natural congeners have been further investigated. Consequently, a campaign was formulated to obtain this trio of compounds. A second goal was to explore a University of California Santa Cruz (UCSC) repository sample (*Z. fuliginosa*, coll. no. 93132) having semi-pure fractions with PANC-1 selective cytotoxicity. Its methanol-soluble fraction, coded DMM, exhibited an inhibitory zone differential of 8 cm between PANC-1 cells and "normal" CFU-GM cells at 180 µg per disk. NMR and LCMS evaluation of the crude extracts implied that four compounds could be obtained including makaluvamines C (2), D (7), J (9) and damirone A (5). While a multi-milligram sample of makaluvamine H (4) was available from the UCSC repository, there were no samples of makaluvamine I available.

Isolation work on the sample (coll. no. 93132) described above provided 10 mg of makaluvamine C (9). It was predicted that other compounds could be efficiently obtained once a repertoire of makaluvamine-containing *Z. fuliginosa* sponges was assembled; this was successfully achieved and summarized in FIG. 2 along with a representative underwater photograph of *Z. fuliginosa*. There were 33 samples in total; the UCSC repository was the source of 15 of these and 18 were provided from the National Cancer Institute-Developmental Therapeutics Program (NCI-DTP) branch. Overall, these sponges were collected from more than four major Indo-Pacific zones and six of these samples, chosen to reflect diverse Indo-Pacific collection locales, were selected for further work-up.

The work flow on the six samples shown in FIG. 2 proceeded and subsequently provided compounds 1-12 (FIG. 3) all containing the pyrrolo[4,3,2-de]quinoline core (FIG. 1). Details of the isolation results are shown in FIGS. 9-13. Highlights of the dereplication steps, including $^1$H NMR and MS$^2$ data are discussed below. The sustained work on these samples provided large multi-milligram quantities of four compounds: makaluvamine C (2)=72 mg, damirone B (3)=102 mg, makaluvamine D (7)=61 mg, and makaluvamine J (9)=118 mg; smaller amounts of seven compounds were also obtained: makaluvamine A (1)=30 mg, damirone A (5)=14 mg, damirone D (6)=4 mg, makaluvamine G (8)=14 mg, makaluvamine K (10)=38 mg, makaluvamine L (11)=11 mg, and makaluvamine P (12)=17 mg.

Example 2—Dereplicating Pyrrolo[4,3,2-de]quinolines Using MS$^2$ Patterns

Figure 4:
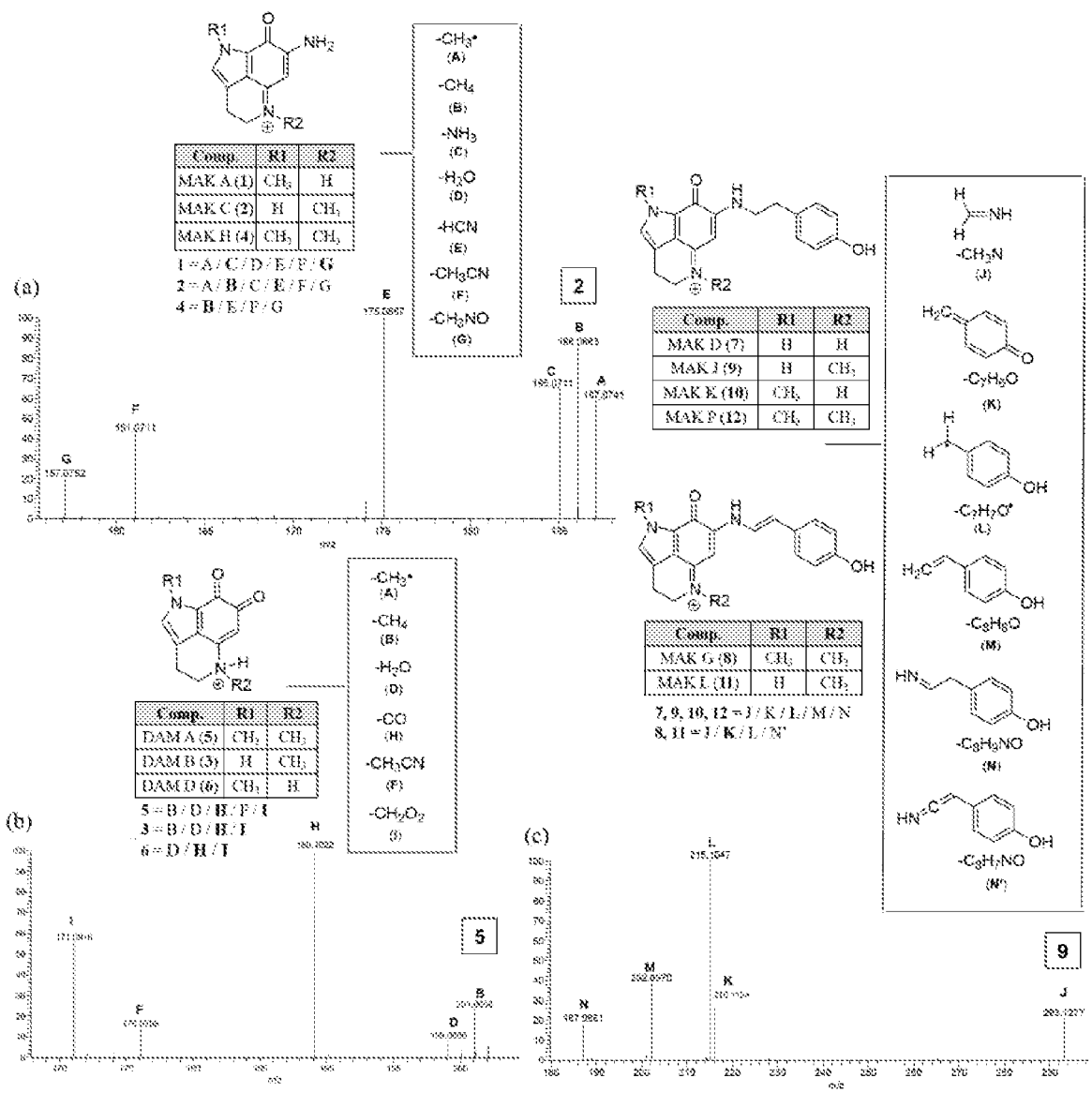
FIG. 4 shows Scheme 1. Makaluvamine and damirone $MS^2$ fragmentation ions diagnostic for N-alkyl substitutions on the pyrrolo[4,3,2-de]quinoline core of the family. Annotated peaks, especially intense m/z ions in bold, represent a signature fingerprint. The panels (a) & (c) illustrate fragmentations for iminocyclohexadienones (example MAK C (2) and MAK J (9)) and panel (b) shows fragmentation for aminocyclohexadienediones (example DAM A (5).

Employing only $^1$H NMR data to engage in rapid dereplication of a pyrrolo[4,3,2-de]quinolines can be challenging. The major problem is that the resonances that might be used to characterize the core skeleton are not rich with information; signals for five to six distinct protons assignable to this core (FIG. 16) are either singlet or triplet resonances, which does not allow making interconnections between isolated spin systems. Consequently, data was sought from high accuracy mass spectrometry (HAMS) m/z ions produced through MS$^2$ runs. Aside from a lone MS-MS study on synthetic makaluvamine analogs, FBA-TPQ/PEA-TPQ [25], no such data can be found in the literature. Consequently, as each compound was purified and analyzed by $^1$H NMR, the data set was expanded to include MS$^2$ analysis. Typical results are shown in FIG. 4 and diagnostic patterns could be identified as discussed further below.

Distinct MS$^2$ fingerprints (FIG. 4) resulted from the loss of specific functional groups from the parent ions depending on the class of compound. The functional groups were coded with specific letters (A-N) and the MS$^2$ peaks that correspond to the parent mass minus that functional group are labeled with that letter code. There were four distinct MS$^2$ fingerprints that arose from 1-12. The first was observed from the makaluvamines that did not contain a N-aryl phenol substituent off the B-ring, A (1), C (2) and H (4) (FIG. 4a). These compounds generated MS$^2$ fragments that corresponded to the loss of the following functional groups: $CH_3$· (A), $CH_4$ (B), $NH_3$ (C), $H_2O$ (D), HCN (E), $CH_3CN$ (F), and $CH_3NO$ (G). The most intense of which were the loss of C from 1, E from 2, and B from 4. The second fingerprint observed was from the damirones B (3), A (5), and D (6) (FIG. 4b), these compounds generated fragments that resulted from the loss of similar groups as 1, 2, and 4 such as A, B, D, and F. However, the most intense fragments resulted from the loss of CO (H) and $CH_2O_2$ (I), two fragmentation ions that did not arise from any of the makaluvamine analogs and were diagnostic of the damirone ring core. The third MS$^2$ fingerprint observed was from D (7), J (9), K (10), and P (12), the makaluvamines with a 4-ethyl phenol substituent off the B-ring (FIG. 4c). These compounds had identical MS$^2$ fingerprints that arose from the loss of $CH_3N$ (J), $C_7C_6O$ (K), $C_7H_7O$. (L), $C_8H_8O$ (M), and $C_8H_9NO$ (N), with the most intense ion resulting from the loss of L. The last MS$^2$ fingerprint observed in this study arose from G (8) and L (11), the makaluvamines with a 4-ethenyl phenol substituent off the B-ring. The MS$^2$ fingerprints from 8 and 11 arose from the loss of E, K, L, and a reduced form of N (N'), with the most intense ion resulting from the loss of K.

Once these distinct MS$^2$ fingerprints were understood it became possible to engage in MS$^2$-driven dereplication and quickly identify 1-12 in *Z. fuliginosa* extracts. For example, 1 and 2 have the same m/z but different fragmentation ion ratios, in that the major fragment from 1 is C and 2 is E, the same is true of 3 and 6, where 3 generates a B fragment and 6 does not. Additionally, the loss of H and I from the damirones (3, 5, and 6) made these readily identifiable from the makaluvamines without substituents off the B-ring (1, 2, and 4) compounds that are otherwise similar in mass and $^1$H-NMR signals. All MS$^2$ spectra and predicted fragmentation structures are shown in Appendix A of U.S. Provisional Patent Application No. 62/471,261 and Lin et al. (2017) *Marine Drugs* 15:98 (FIGS. S17-S31) along with a summary of the makaluvamine and damirone analogs present in some of the *Z. fuliginosa* extracts in the UCSC repository (Table S2 of Appendix A of U.S. Provisional Patent Application No. 62/471,261 and Lin et al. (2017) *Marine Drugs* 15:98, the disclosures of which are incorporated herein by reference in their entireties for all purposes).

Example 3—Semi-Synthesis of Acetylated Makaluvamines and their Identification Using $^1$H NMR and MS$^2$ Data To determine whether the makaluvamines could be candidates for further clinical development as antibody drug conjugates (ADC), it was desirable to ensure that the addition of a functional group to the amide or N-alkyl phenol would not result in the loss of cytotoxic activity.

Figure 5:
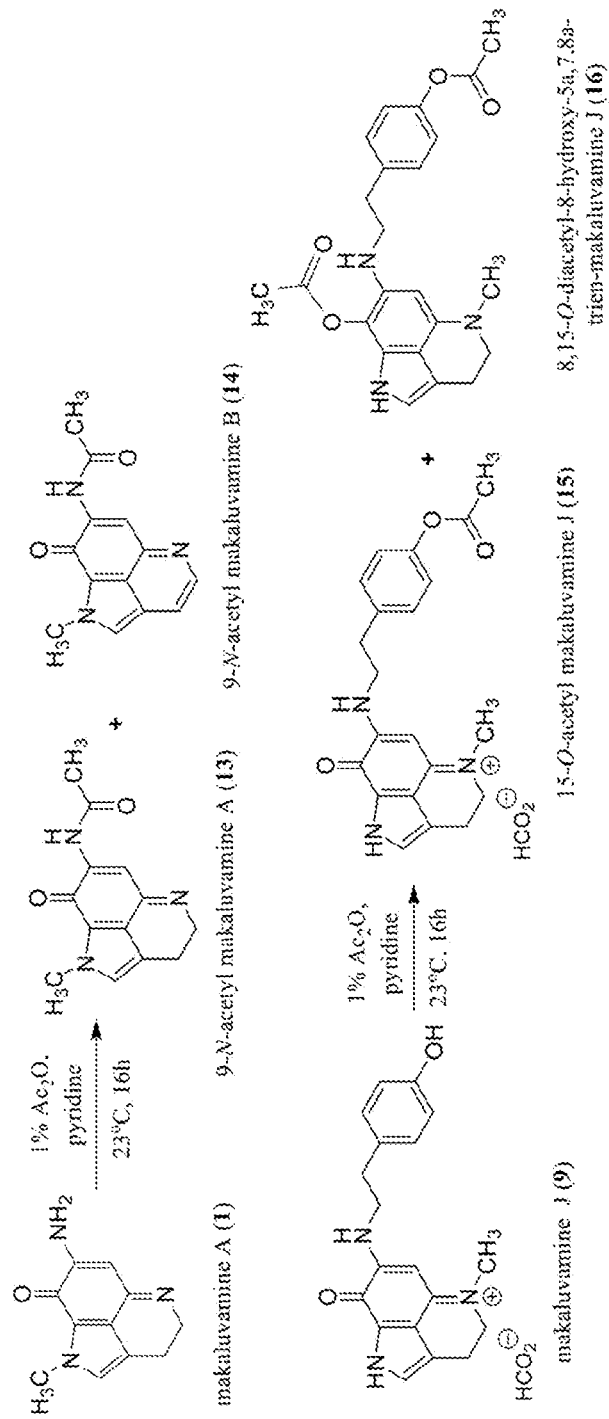
FIG. 5 shows Scheme 2. Outcomes of the acetylation of makaluvamines A (1) and J (9).

Therefore acetylated derivatives were prepared from makaluvamine A (1) and J (9) (FIG. 5). The acetylation of 1 (Scheme S6 of Appendix A of U.S. Provisional Patent Application No. 62/471,261 and Lin et al. (2017) *Marine Drugs* 15:98) with acetic anhydride in pyridine resulted in the production of 9-N-acetyl makaluvamine A (13). The structure of 13 was confirmed by HAESIMS and MS$^2$ data in addition to comparison of its $^1$H-NMR spectrum to that of 1. The HAESIMS supported a molecular formula of $C_{13}H_{13}N_3O_2$, and the MS$^2$ fingerprint (FIG. S29 of Appendix A of U.S. Provisional Patent Application No. 62/471,261 and Lin et al. (2017) *Marine Drugs* 15:98) contained a fragment corresponding to the loss of the acetyl group to give 1. Comparison of the $^1$H-NMR spectra (Table 1; FIGS. S1 & S13 of Appendix A of U.S. Provisional Patent Application No. 62/471,261 and Lin et al. (2017) *Marine Drugs* 15:98) of 1 and 13, showed very little variation with the exception of an additional singlet at δ 2.34 corresponding to the acetate methyl and the downfield shift of the resonance for the proton at position 6 from δ 5.61 to δ 6.31. In addition to 13 the aromatized 9-N-acetyl makaluvamine B (14) were also obtained from the acetylation of 1. The evidence for aromatization in 14 is a marked downfield shift of the resonances for protons 3 and 4 from triplets at δ 2.70 and δ 3.95, to doublets at δ 7.75 and δ 8.43, respectively (Table 1; FIGS. S1 & S14 of Appendix A of U.S. Provisional Patent Application No. 62/471,261 and Lin et al. (2017) *Marine Drugs* 15:98). Additionally, the HAESIMS m/z data supported a molecular formula of $C_{13}H_{11}N_3O_2$ and the MS$^2$ spectrum revealed the loss of the acetyl group resulting in a fragment with the correct m/z for makaluvamine B (FIG. S30 of Appendix A of U.S. Provisional Patent Application No. 62/471,261 and Lin et al. (2017) *Marine Drugs* 15:98).

TABLE 1

$^1$H NMR data for makaluvamines A (1), J (9), and their acetate derivatives (13-16) prepared as shown in Scheme 2.

| position | A (1)$^a$ | A-Ac (13)$^a$ | B-Ac (14)$^b$ | J (9)$^a$ | J-Ac (15)$^a$ | J di-Ac (16)$^b$ |
|---|---|---|---|---|---|---|
| | | | $δ_H$, mult, (J, Hz) | | | |
| 2 | 7.27, s | 7.17, s | 8.15, s | 7.31, s | 7.13, s | 7.32, s |
| 3 | 2.81, t (7.5) | 2.70, t (7.5) | 7.75, d (6.0) | 2.92, t (7.5) | 2.95, brs | 3.04, t (7.5) |
| 4 | 3.77, t (7.5) | 3.95, t (7.5) | 8.43, d (6.0) | 3.89, t (7.5) | 3.78, brs | 3.93, t (7.5) |
| 6 | 5.61, s | 6.31, s | 8.67, s | 5.59, s | 5.42, s | 6.17, s |
| 10 | | | | 3.60, t (7.0) | 3.63, brs | 3.76, t (7.5) |
| 11 | | | | 2.83, t (7.0) | 2.85, brs | 2.98, t (7.5) |
| 13 | | | | 7.05, d (8.0) | 7.05, d (8.0) | 7.03, d (8.0) |
| 14 | | | | 6.69, d (8.0) | 7.29, d (8.0) | 7.31, d (8.0) |
| N1—Me | 3.89, s | 3.83, s | 4.39, s | | | |
| N5—Me | | | | 3.37, s | 3.28, s | 3.31, s |

TABLE 1-continued $^1$H NMR data for makaluvamines A (1), J (9), and their acetate derivatives (13-16) prepared as shown in Scheme 2.

| position | A (1)$^a$ | A-Ac (13)$^a$ | B-Ac (14)$^b$ | J (9)$^a$ | J-Ac (15)$^a$ | J di-Ac (16)$^b$ |
|---|---|---|---|---|---|---|
| | | | $δ_H$, mult, (J, Hz) | | | |
| Ac | | 2.34, s | 2.26, s | | 2.25 | 2.27, s 2.09, s |

$^a$$^1$H NMR data measured in DMSO-d$_6$ at 500 MHz;
$^b$$^1$H NMR data measured in CD$_3$OD at 600 MHz Attempts to acetylate makaluvamine C (2) proved unsuccessful, perhaps due to the presence of the methyl at position N-5 hindering the aromatization of the C-ring. However the presence of the N-5 methyl did not hinder the acetylation of the B-ring carbonyl or 4-ethyl phenol substituent as was seen by the successful acetylation of 9 (FIG. 16) which yielded 15-O-acetyl makaluvamine J (15) and 8,15-O-di-acetyl-8-hydroxy-5a,7,8a-trien-makaluvamine J (16). The structure of 15 was confirmed by HAESIMS and MS$^2$ fingerprint (FIG. 15). The observed m/z supports a molecular formula of $C_{21}H_{22}N_3O_3$ for the cation, and the MS$^2$ fragments observed corresponding to the loss of an acetyl plus J, L, M, and N. This fragmentation pattern is similar to the MS$^2$ fingerprint of 9 (FIG. 4, panel c), which could only be observed if the acetyl group was on the 4-ethyl phenol substituent. Furthermore, there was little variation between the $^1$H-NMR spectra of 9 and 15 aside from the appearance of the methyl acetate singlet at δ 2.25 and the downfield shift for the resonance of protons at position 14 from δ 6.69 to δ 7.29 (Table 1; FIGS. S9 & S15 of Appendix A of U.S. Provisional Patent Application No. 62/471,261 and Lin et al. (2017) *Marine Drugs* 15:98). The HAESIMS of 16 confirmed a molecular formula of $C_{23}H_{25}N_3O_4$, and the MS$^2$ fingerprint yielded fragments consistent with those predicted for 9 with acetyl groups on both the B-ring carbonyl and 4-ethyl phenol (FIG. S32 of Appendix A of U.S. Provisional Patent Application No. 62/471,261 and Lin et al. (2017) *Marine Drugs* 15:98). This is further confirmed by comparison of the $^1$H NMR of 16 to 9 where the spectrum of 16 shows the presence of two methyl acetate singlets at δ 2.09 and δ 2.27 and a downfield shift of the resonance for the proton at position 6 from δ 5.59 to δ 6.17 (Table 1; FIGS. S9 & S16 of Appendix A of U.S. Provisional Patent Application No. 62/471,261 and Lin et al. (2017) *Marine Drugs* 15:98). While the presence of the N-5 methyl hindered the acetylation of 2, its presence along with the absence of the N-1 methyl appear to be critical in the acetylation of makaluvamines containing a 4-ethyl phenol substituent as 9 was the only one to be successfully acetylated under the conditions used in this study.

Example 4—Evaluating Cytotoxicity Data for a Mini-Library of 22 Compounds

The task of IC$_{50}$ assessment for the natural products isolated in this study against the PANC-1 tumor cells line began immediately following the purification and characterization of each pyrrolo[4,3,2-de]quinoline obtained (FIG. 3). Sufficient amounts for assay screening were obtained for analogues 1-12 and three additional semisynthetic acetates 14-16 (FIG. 3) were prepared from makaluvamines A (1) and J (9). Attempts to obtain other related compounds, based on frameworks shown in FIG. 1, from US academic colleagues, were largely unsuccessful. However, a sample of ammosamide B (17) was obtained from the NCI Molecular Targets Laboratory. Two additional clinically used compounds, etoposide and teniposide [29] were also run in the assay. Finally, literature or unpublished data was retrieved for four molecules: FBA-TPQ (18) [25], isobatzelline C (19) [26], discorhabdin C (20) [unpublished NCI-DTP], and gemcitabine [30]. Several insights can be gained through closer examination of these data shown in Table 2.

The $IC_{50}$ values against PANC-1 are spread out and range from 0.04 µM for teniposide, a chemotherapy drug acting as a topoisomerase II inhibitor, to 26 µM for ammosamide B (17), a cell cycle modulator that targets myosin [19]. For the natural makaluvamines, the $IC_{50}$ values ranged from 0.054 µM for makaluvamine J (9) to 6.2 µM for makaluvamine G (8), over a 100-fold difference in potency. As for the semi-symthetic analogs from makaluvamine A (1), not enough 9-N-acetyl makaluvamine A (13) was obtained for $IC_{50}$ determination, but the $IC_{50}$ of 9-N-acetyl makaluvamine B (14) was 91 µM, over a 200-fold reduction in potency vs. that of 1 ($IC_{50}$=0.45 µM). There was greater success from one of the semi-synthetic analogs obtained from 9, the acetate deriviative 15-O-acetyl makaluvamine J (15) retained the double digit nanomolar potency ($IC_{50}$=0.081 µM) observed from 9, making it a viable candidate for further clinical development as an ADC. By contrast, the di-acetate compound, 8,15-O-diacetyl-8-hydroxy-5a,7,8a-trien-makaluvamine J (16), was triple digit nanomolar ($IC_{50}$=0.59 µM) in potency making it not of priority for further studies. Based on the PANC-1 $IC_{50}$ data set, makaluvamine J (9) and 15-O-acetyl makaluvamine J (15) were selected for additional $IC_{50}$ determination against the human ovarian cancer cell line, OVCAR-5. Makaluvamine J (9) had an $IC_{50}$ value of 120 nM which was similar in potency to reported valued for other pyrrolo[4,3,2-de]quinoline containing compounds against OVCAR-3 and OVCAR-5 cell lines (Table 2). Strikingly, the addition of the acetyl group on 15 resulted in a 14-fold increase in potency over 9 with single digit nanomolar potency of 8.6 nM against OVCAR-5. In summary, compounds 9 and 15 exhibit the most potent $IC_{50}$ values relative to all other natural and synthetic makaluvamine analogs studied to date. Sought was a deeper understanding of the structural features responsible for the wide range of $IC_{50}$ data shown in Table 2.

TABLE 2

$IC_{50}$ data for pyrrolo[4,3,2-de]quinolines and therapeutic standards against ovarian and pancreatic cancer tumor cell lines.

| Compound | PANC-1 $IC_{50}$ (µM) | OVCAR-3/-5 $IC_{50}$ (µM) |
|---|---|---|
| makaluvamine A (1) | 0.45 | |
| makaluvamine C (2) | 0.73 | 0.24[a]/NT |
| damirone B (3) | 19 | |
| makaluvamine H (4) | 3.6 | 0.96[a]/0.10[a] |
| damirone A (5) | 160 | |
| damirone D (6) | 3.4 | |
| makaluvamine D (7) | 0.29 | |
| makaluvamine G (8) | 6.2 | |
| makaluvamine J (9) | 0.054 | NT/0.12 |
| makaluvamine K (10) | 0.56 | |
| makaluvamine L (11) | 1.9 | |
| makaluvamine P (12) | 0.3 | |
| 9-N-acetyl makaluvamine B (14) | 91 | |
| 15-O-acetyl makaluvamine J (15) | 0.081 | NT/0.0086 |
| 8,15-O-diacetyl-8-hydroxy-5a,7,8a-trien-makaluvamine J (16) | 0.59 | |
| ammosamide B (17) | 26 | |
| FBA-TBQ (18) | 0.11[b] | 0.95[c]/NT |
| isobatzelline C (19) | 10[d] | |

TABLE 2-continued $IC_{50}$ data for pyrrolo[4,3,2-de]quinolines and therapeutic standards against ovarian and pancreatic cancer tumor cell lines.

| Compound | PANC-1 $IC_{50}$ (µM) | OVCAR-3/-5 $IC_{50}$ (µM) |
|---|---|---|
| discorhabdin C (20) | NT | 0.33[e]/2.6[e] |
| etoposide | 0.39 | |
| teniposide | 0.041 | |
| gemcitabine | 7.2[f] | |

NT = Not Tested;
Refs:
[a]data obtained from Dijoux et al [9];
[b]data obtained from Zhang et al. [25];
[c]data obtained from Chen et al., 2011 [38];
[d]data obtained from Guzmán et al. [26];
[e]data obtained from the NCI-DTP 60 Human Tumor Cell Lines Database;
[f]data obtained from Li et al. [30].

Example 5—Assessing Relative PANC-1 Potencies of Pyrrolo[4,3,2-de]quinolines

Figure 6:
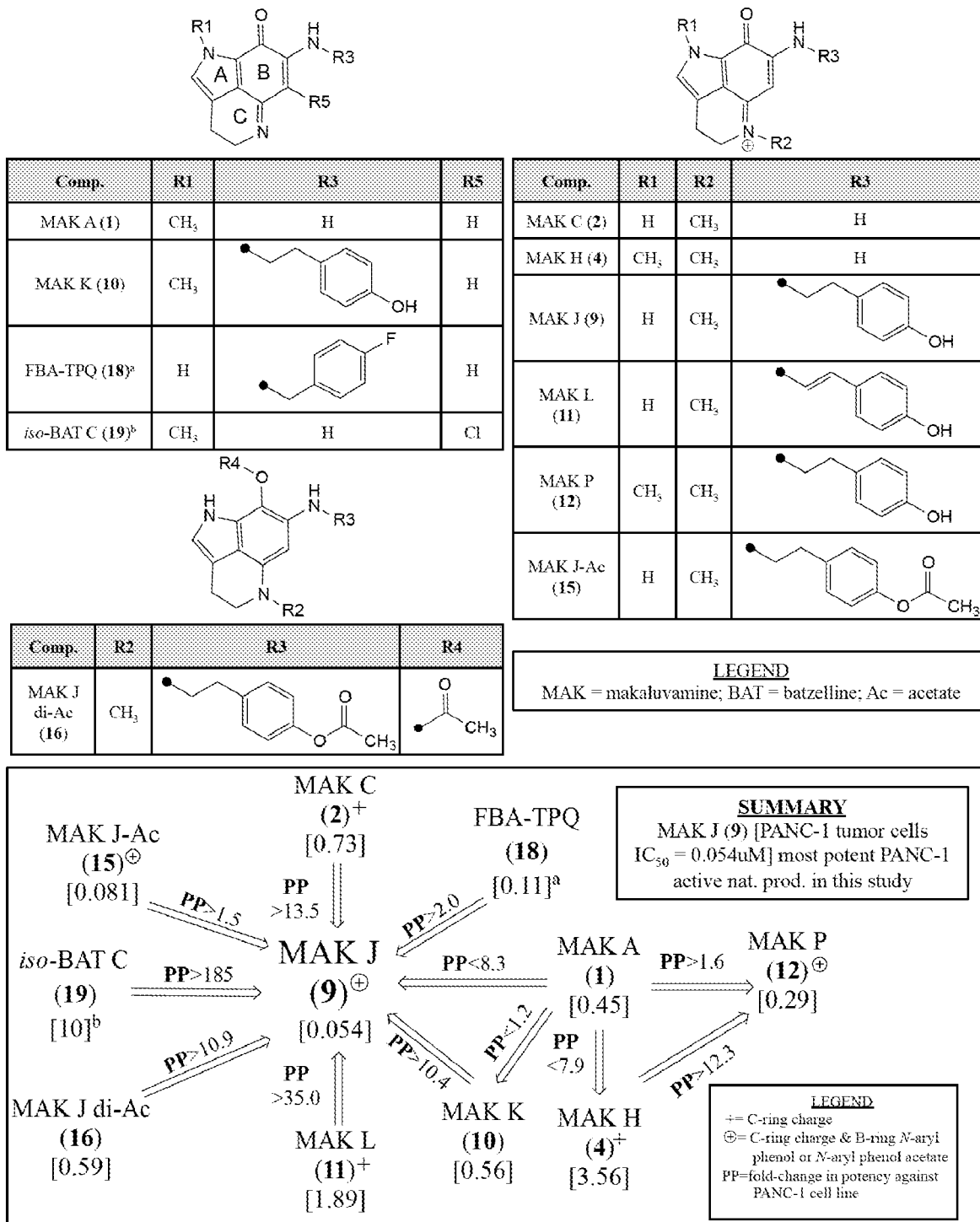
FIG. 6 shows the impact of on relative in vitro $IC_{50}$ Potencies [μM] against PANC-1 (coded by PP, with inc>, dec<) as a function of: (i) ABC-ring conjugation, (ii) $^+$C-ring charge, and (iii) $^+$C-ring charge with a B-ring 4-ethyl phenol or 4-ethyl phenol acetate substituent for pyrrolo[4,3,2-de] quinolone containing molecules. Refs: $^a$data obtained from Zhang et al. [25]; $^b$data obtained from Guzman et al. [26].

The quantitative responses of selected compounds against the PANC-1 cell line provide a fresh perspective to plan additional preclinical campaigns based on the makaluvamine framework. The $IC_{50}$ variations for 12 makaluvamine analogs (1, 2, 4, 7-12, 14-16), one related halogenated compound, isobatzelline C (19) [26], and the synthetic compound, FBA-TPQ (18) [25] represent an important learning set. Even though all the entries of FIG. 6 contain an ABC-ring pyrroloiminoquinone core, a wide range of PANC-1 $IC_{50}$'s are represented; makaluvamine J (9) being the most potent and 19 being relatively inactive. The substituent variations on the tricyclic core shown at the top of FIG. 6 are key to review as follows. There are changes at: (i) R1 ($CH_3$ or H) on the A-ring, (ii) R2 ($CH_3$) on the C-ring (note the + charge at the nitrogen), and (iii) R3 (H, 4-ethyl phenol substituent, 4-ethenyl phenol substituent, 4-ethyl phenol acetate substituent, or 4-fluorobenzyl substituent). Additional variations occur at: (iv) R4 [C(=O)$CH_3$/acetate] on the B-ring, and (v) R5 (CI) on the B-ring of isobatzelline C (19) [26]. The inset panel of FIG. 6 illustrates the relative impact of these substituent changes on the in vitro $IC_{50}$ Potencies [µM] against PANC-1. This impact is coded as PP with an increase in potency indicated by ">" and a decrease in potency indicated by "<". Three relevant SAR structural motifs to note are (i) ABC-ring conjugation; (ii) a C-ring charge coded as "+"; and (iii) a C-ring charge and a B-ring 4-ethyl phenol or 4-ethyl phenol acetate substituent coded as "⊕".

The boxed panel in FIG. 6 highlights that makaluvamine J (9), with code "⊕" indicating a C-ring charge and a B-ring 4-ethyl phenol substituent is the most potent against PANC-1, exhibiting an $IC_{50}$ of 0.054 µM. The designed synthetic compound, FBA-TPQ (18) [25], without a positive C-ring charge and a 4-fluorobenzyl substituent, is ~50% less potent than 9 with an $IC_{50}$ of 0.11 µM. 15-O-acetyl makaluvamine J (15) which only differs from 9 by the addition of an acetyl group on the R3 substituent is only slightly less potent (PP<1.5) than 9 with an $IC_{50}$ of 0.081 µM. However, the diacetyl makaluvamine J (16) which differs in having an aromatized B-ring and substituents at position R3 and R4, is ~10 fold less potent than 9 as it has different ABC-ring conjugation and no positive charge on the C-ring. Additionally, when comparing 9 and makaluvamine K (10) which only differ in their N-methyl position (9 R1=H, R2=$CH_3$; 10 R1=$CH_3$, R2=none, no + charge on C-ring) there is a 10.4 fold decrease in potency, further indicating that the presence of the positive charge on the C-ring is important for potency.

Shown in FIG. 6 are the functional group patterns required for the impressive PANC-1 potency of 9 that has R1=H, R2=CH$_3$, R3=4-ethyl phenol. Specifically, less potency was observed for the substitution patterns present in makaluvamine C (2) (R1=H, R2=CH$_3$, R3=H) and makaluvamine L (11) (R1=H, R2=CH$_3$, R3=4-ethenyl phenol). Which resulted in reduced potency compared to 9 with decreases in PP of 13.5 and 35.0, respectively. This highlights that the presence of an N-aryl substituent at R3 is important for increase potency against PANC-1, but that the flexibility of that substituent is also important as the ethyl phenol analogs (D (7), J (9), K (10), and (P) 12) show greater potency that the ethenyl phenol analogs (G (8), L (11)). A comparison of makaluvamines A (1) and K (10) which only differ at R3 (1 R3=H; 10 R3=4-ethyl phenol) show minimal difference in potency (PP<1.2). However, when comparing 1 to makaluvamine H (4), which only differ at R2 (1 no R2; 4 R2=CH$_3$), a greater reduction in potency is observed (PP<7.9). Notably, when comparing 4 to makaluvamine P (12), which only differ at R3 (4 R3=H; 12 R3=4-ethyl phenol), there is a markedly greater increase in potency (PP>12.3), further confirming that the presence of an N-aryl substituent is important for potency. In summary, the SAR trends of FIG. 6 support the selection of 9 and 15 for future development.

Example 6—Secondary Screening

Data summarized above (Table 2, FIG. 6) led to the next steps of secondary screening on the prioritized compound, makaluvamine J (9). The first follow-up experiments have been completed and utilized a clonogenic assay to assess cell survival through data plotted as a concentration-survival curve [31]. Sponge-derived compounds from previous work by the inventors have shown a favorable profile in such evaluations and include: fascaplysin A [32], fijianolide B [33], japlakinolide [31] and psymberin [34].

Figure 7:
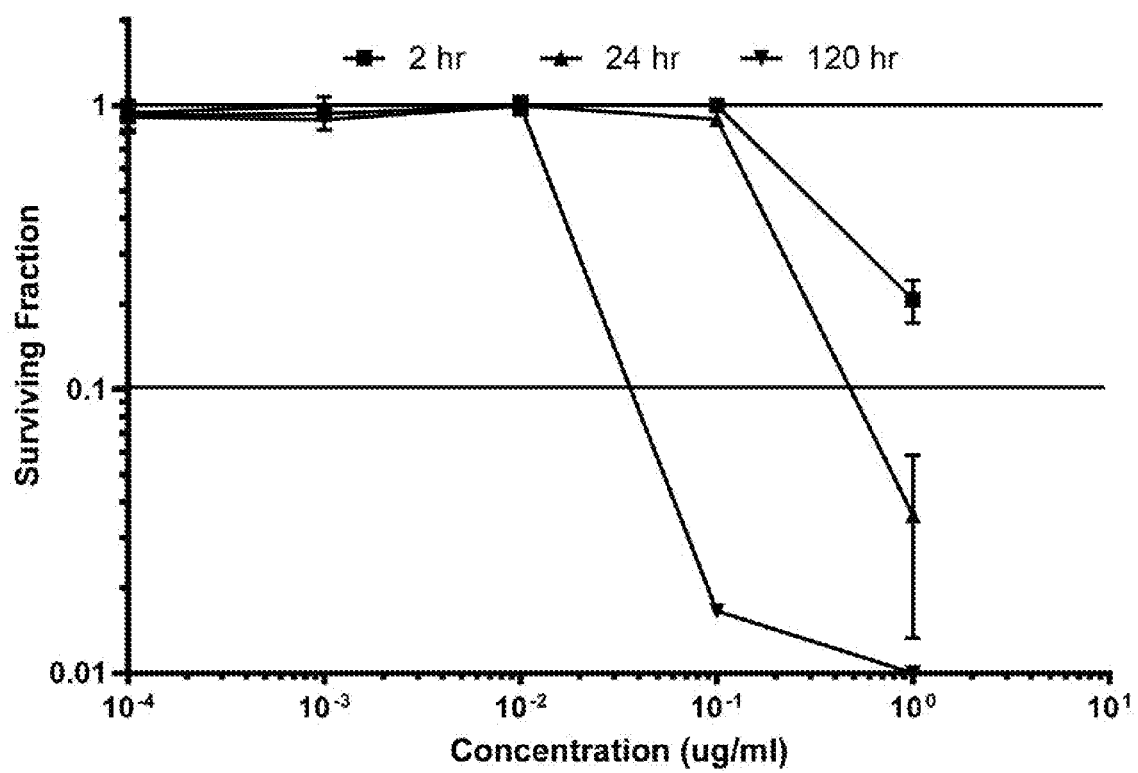
FIG. 7 Evaluation of makaluvamine J (9) through clonogenic dose-response evaluation employing HCT-116 cells. Continuous exposure of the cells with 9 at different concentrations during periods of: 2 hr, 24 hr, or 120 hr. Efficacy is indicated when the surviving fraction is less than 0.1.
Figure 8:
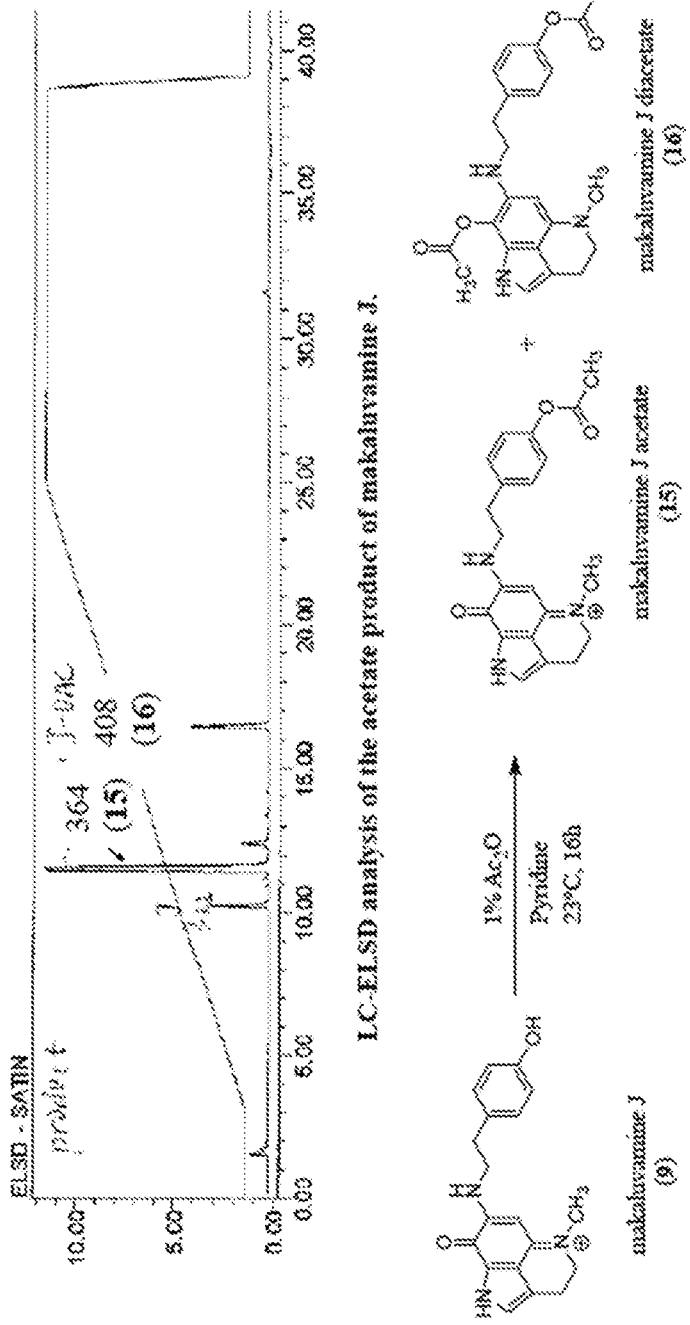
FIG. 8 The acetylation reaction of makaluvamine J (9).

Accurate determination of the exposures required to achieve a useful in vivo therapeutic effect is the outcome being sought through clonogenic study. Illustrated here are data measuring the cytotoxic effect of makaluvamine J (9) at varying concentrations during continuous exposure. Other relevant data to be obtained in the future consists of: (a) repeating the clonogenic runs on makaluvamine acetate J (15), (b) obtaining the maximum tolerated dose (MTD) for both, and (c) assessing the pharmacokinetic behavior of these compounds measured in both plasma and tumors, (PANC-1 and OVC-5) at the MTD which will be tracked through by MS$^2$ data. Results from the clonogenic assay of makaluvamine J (9) are shown in FIG. 7. The key measurement involved determining the required time-concentration profile to obtain a 90% kill (10% survival-S$_{10}$) of tumor cells. Little toxicity to HCT-116 cells was shown at the two hour dosing schedule; and effects observed are as follows: (i) 2 h exposure, $_2$S$_{10}$=3 µg/mL (extrapolated); (ii) 24 h exposure, $_{24}$S$_{10}$=400 ng/mL; and (iii) 120 h exposure, $_{120}$S$_{10}$-10=30 ng/mL. These results are very promising and predict success in the follow up evaluations with PANC-1 and OVCAR-5 tumors. At this juncture it appears that a chronic exposure for five days will be effective and the exact therapeutics regime will depend on the MTD determination data and future pharmacokinetic results. Once these results are in hand, the necessary drug dose and schedule required to achieve a positive in vivo therapeutic effect will be fully defined [35].

Materials and Methods
General Experimental Procedures

Standard pulse sequences were used for all NMR experiments, which were run on either a Varian UNITY INOVA spectrometer (600 MHz for $^1$H) outfitted with a 5 mm triple resonance (HCN) cold probe, a Varian spectrometer (500 MHz for $^1$H) equipped with an inverse detection probe, or a Bruker spectrometer (800 MHz for $^1$H) outfitted with a 5 mm triple resonance (HCN) inverse cold probe. Residual solvent shifts for DMSO-d$_6$ or CD$_3$OD were referenced to $\delta_H$ 2.50 or $\delta_H$ 3.31, respectively. Accurate mass measurements for molecular formula determinations were obtained on a Thermo Velos Pro electrospray ionization hybrid ion trap-Orbitrap mass spectrometer. All HPLC was done in reversed-phase (RP) and utilized HPLC grade CH$_3$CN (solvent A) and Milli-Q H$_2$O (solvent B), both adjusted to contain 0.1% formic acid (Fisher Chemical). The analytical LC-MS system was composed of Waters HPLC components (i.e., solvent pumps and autosampler) and controlled by Empower software (Waters). A 150×4.60 mm 5 µm Luna C18 column (Phenomenex) was utilized, and the system operated at a flow rate of 1 mL/min. The eluent first passed through a photodiode array (Waters) and then was split (95:5) between an evaporative light-scattering detector (ELSD) (SEDEX model 75) and an ESITOF mass spectrometer (Applied Biosystems Mariner). Column chromatography (CC) was performed using Sephadex LH-20 (40-70 µm; Amersham Pharmacia Biotech AB, Uppsala, Sweden) with MeOH as eluent. The preparative RP-HPLC system was composed of Waters HPLC components (i.e., solvent pumps and gradient controller) and equipped with a 250×21 mm 10 µm Synergi MAX-RP column (Phenomenex) and Pharmacia LKB UV-absorbance detector.

Animal Material

Figure 2:
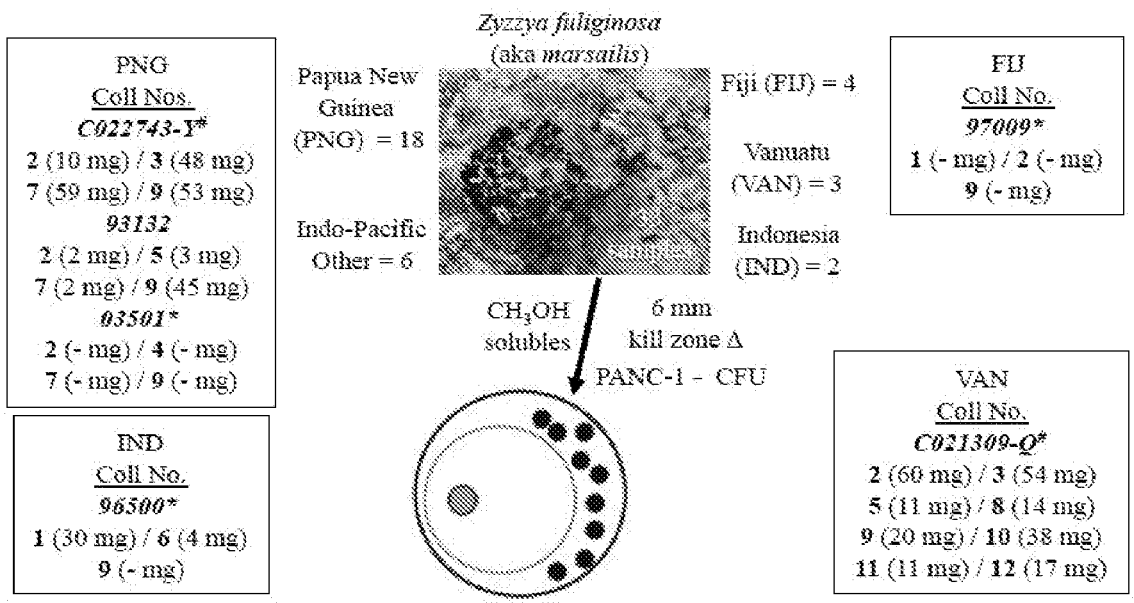
FIG. 2 *Zyzzya fuliginosa* sponges for the isolation campaign of their cytotoxic pyrrolo[4,3,2-de]quinoline constituents (1-12). Six of the 33 repository samples available were extensively investigated using *University of California Santa Cruz and #NCI-DTP material.

Specimens of Z. fuliginosa were collected from Papua New Guinea (PNG) (coll. nos. 93132, 1.8 kg wet wt. and 03501, 1.2 kg wet wt.), Indonesia (96500; 1.2 kg wet wt.), and Fiji (97009; 1.9 kg wet wt.) using SCUBA at depths between 15-30 m by members of the UCSC team, a representative underwater photograph of this organism is shown in FIG. 2. Two Z. fuliginosa extracts, obtained from the NCI-DTP repository were collected from PNG (C022743-Y) and Vanuatu (C021309-Q).

Extraction and Isolation

Z. fuliginosa samples collected by the UCSC laboratories (coll. nos. 93132, 96500, 03501, and 97009) were preserved in the field and subsequently extracted using either a standard solvent partition (SSP) or an accelerated solvent extraction (ASE) according to previously described protocols [36]. Extracts obtained from the NCI-DTP collection (coll. nos. C021309-Q and C022743-Y) were processed according to NCI protocol [37]. Semi-pure extracted fractions that exhibited selective bioactivity against the PANC-1 cell line were further purified.

Samples coded as 93132 (FIG. 9) and 96500 (FIG. 10) were extracted using the SSP method and the dichloromethane-methanol fraction (coded DMM) contained bioactivity against the PANC-1 cell line. The DMM fractions were further divided into four fractions using preparative HPLC (10:90 CH$_3$CN:H$_2$O to 100% CH$_3$CN, 35 min) and labeled H1-H4. From sample 93132, the DMM-H4 fraction was subjected to CC to yield makaluvamine D (7) (2 mg) and makaluvamine J (9) (45 mg). The DMM-H2 and DMM-H3 fractions were further purified by HPLC (5:95 CH$_3$CN:H$_2$O to 60:40 CH$_3$CN:H$_2$O, with 0.1% formic acid) to yield makaluvamine C (2) (2 mg) and damirone D (5) (3 mg), respectively. From sample 96500, the DMM-H2 and DMM- H3 fractions were further purified by CC to yield makaluvamine A (1) (30 mg) and damirone D (6) (4 mg), respectively.

Two NCI-DTP extracts coded C021309-Q (FIG. 11) and C022743-Y (FIG. 12) were subjected to CC and divided into seven fractions labeled F1-F7. Workup on the first sample C021309-Q (FIG. 11), began with the F1 and F2 fractions and involved purification by HPLC (5:95 $CH_3CN:H_2O$ to 60:40 $CH_3CN:H_2O$, with 0.1% formic acid) to yield makaluvamine P (12) (17 mg) and 5 (11 mg), respectively. The F3 fraction was subjected to the same HPLC conditions as fractions F1 and F2 to give 2 (60 mg), damirone B (3) (54 mg), and makaluvamine G (8) (14 mg). The F3-H4 fraction was further separated by HPLC (20:80 $CH_3CN:H_2O$ to 35:65 $CH_3CN:H_2O$, with 0.1% formic acid) to yield 9 (20 mg) and makaluvamine K (10) (38 mg). The F4 and F5 fractions were combined and purified by HPLC (5:95 $CH_3CN:H_2O$ to 50:50 $CH_3CN:H_2O$, with 0.1% formic acid) to yield makaluvamine L (11) (11 mg). Workup on the second sample C022743-Y (FIG. 12) began with the F2 fraction using HPLC (5:95 $CH_3CN:H_2O$ to 60:40 $CH_3CN:H_2O$, with 0.1% formic acid) to yield 9 (53 mg). The F3 fraction was also subjected to the same HPLC condition as F2 to give 2 (10 mg), 3 (33 mg), and 7 (21 mg). The F4 fraction was purified by HPLC (5:95 $CH_3CN:H_2O$ to 50:50 $CH_3CN:H_2O$ with 0.1% formic acid) to yield 3 (15 mg) and 7 (32 mg), and the F5 fraction contained only 7 (6 mg). In total the four *Z. fuliginosa* extracts generated 30 mg of 1, 72 mg of 2, 102 mg of 3, 14 mg of 5, 4 mg of 6, 61 mg of 7, 14 mg of 8, 118 mg of 9, 38 mg of 10, 11 mg of 11, 17 mg of 12.

Two additional samples 03501 and 97009 (FIG. 13) were each extracted using the ASE method and the methanol extracts (coded XFM) were determined to have selective bioactivity against the PANC-1 cell line. LCMS analysis was used to identify 2, makaluvamine H (4), 7, and 9 in the 03501-XFM fraction [36] and 1, 2, and 9 in the 97009-XFM fraction. In summary 12 known compounds (1-12) shown in FIG. 3 were obtained and dereplicated by comparing their properties to those in the literature.

Compound Properties

Makaluvamine A (1): Red-brown solid; $^1$H NMR (DMSO-$d_6$, 500 MHz) data, see FIG. 16 and FIG. S1 in Appendix A of U.S. Provisional Patent Application No. 62/471,261 and Lin et al. (2017) *Marine Drugs* 15:98; HAESIMS m/z [M+H]$^+$ 202.0977 (calcd for $C_{11}H_{12}N_3O$, 202.0975).

Makaluvamine C (2): Red-brown solid; $^1$H NMR (DMSO-$d_6$, 500 MHz) data, see FIG. 16 and FIG. S2 in Appendix A of U.S. Provisional Patent Application No. 62/471,261 and Lin et al. (2017) *Marine Drugs* 15:98; HAESIMS m/z M$^+$ 202.0978 (calcd for $C_{11}H_{12}N_3O$, 202.0975).

Damirone B (3): Red-brown solid; $^1$H NMR (DMSO-$d_6$, 600 MHz) data, see FIG. 16 and FIG. S3 in Appendix A of U.S. Provisional Patent Application No. 62/471,261 and Lin et al. (2017) *Marine Drugs* 15:98; HAESIMS m/z [M+H]$^+$ 203.0813 (calcd for $C_{11}H_{11}N_2O_2$, 203.0810).

Makaluvamine H (4): Sample obtained from the inventors' repository, brown solid; $^1$H NMR (DMSO-$d_6$, 500 MHz) data, see FIG. 16 and FIG. S4 in Appendix A of U.S. Provisional Patent Application No. 62/471,261 and Lin et al. (2017) *Marine Drugs* 15:98; HAESIMS m/z M$^+$ 216.1129 (calcd for $C_{12}H_{14}N_3O$, 216.1131).

Damirone A (5): Red-brown solid; $^1$H NMR (DMSO-$d_6$, 500 MHz) data, see FIG. 16 and FIG. S5 in Appendix A of U.S. Provisional Patent Application No. 62/471,261 and Lin et al. (2017) *Marine Drugs* 15:98; HAESIMS m/z [M+H]$^+$ 217.0974 (calcd for $C_{12}H_{13}N_2O_2$, 217.0972).

Damirone D (6): Red-brown solid; $^1$H NMR (DMSO-$d_6$, 500 MHz) data, see FIG. 16 and FIG. S6 in Appendix A of U.S. Provisional Patent Application No. 62/471,261 and Lin et al. (2017) *Marine Drugs* 15:98; HAESIMS m/z [M+H]$^+$ 203.0817 (calcd for $C_{11}H_{11}N_2O_2$, 203.0815).

Makaluvamine D (7): Red-brown solid; $^1$H NMR (DMSO-$d_6$, 500 MHz) data, see FIG. 16 and FIG. S7 in Appendix A of U.S. Provisional Patent Application No. 62/471,261 and Lin et al. (2017) *Marine Drugs* 15:98; HAESIMS m/z [M+H]$^+$ 308.1396 (calcd for $C_{18}H_{18}N_3O_2$, 308.1394).

Makaluvamine G (8): Green solid; $^1$H NMR (CD$_3$OD, 600 MHz) data, see FIG. 16 and FIG. S8 in Appendix A of U.S. Provisional Patent Application No. 62/471,261 and Lin et al. (2017) *Marine Drugs* 15:98; HAESIMS m/z M$^+$ 334.334.1548 (calcd for $C_{20}H_{20}N_3O_2$, 334.1550).

Makaluvamine J (9): Red-brown solid; $^1$H NMR (DMSO-$d_6$, 500 MHz) data, see FIG. 16 and FIG. S9 in Appendix A of U.S. Provisional Patent Application No. 62/471,261 and Lin et al. (2017) *Marine Drugs* 15:98; HAESIMS m/z M$^+$ 322.1552 (calcd for $C_{19}H_{20}N_3O_2$, 322.1550).

Makaluvamine K (10): Red-brown solid; $^1$H NMR (DMSO-$d_6$, 500 MHz) data, see FIG. 16 and FIG. S10 in Appendix A of U.S. Provisional Patent Application No. 62/471,261 and Lin et al. (2017) *Marine Drugs* 15:98; HAESIMS m/z [M+H]$^+$ 322.1545 (calcd for $C_{19}H_{20}N_3O_2$, 322.1550).

Makaluvamine L (11): Green solid; $^1$H NMR (CD$_3$OD, 500 MHz) data, see FIG. 16 and FIG. S11 in Appendix A of U.S. Provisional Patent Application No. 62/471,261 and Lin et al. (2017) *Marine Drugs* 15:98; HAESIMS m/z M$^+$ 320.1393 (calcd for $C_{19}H_{18}N_3O_2$, 320.1394).

Makaluvamine P (12): Red-brown solid; $^1$H NMR (CD$_3$OD, 500 MHz) data, see FIG. 16 and FIG. S12 in Appendix A of U.S. Provisional Patent Application No. 62/471,261 and Lin et al. (2017) *Marine Drugs* 15:98; HAESIMS m/z M$^+$ 336.1708 (calcd for $C_{20}H_{22}N_3O_2$, 336.1707).

Mass Spectrometry

For each of the makaluvamines and damirones (1-12) the MS and MS$^2$ spectra were obtained using a Thermo Velos Pro-ESI ion trap mass spectrometer using a collision-induced dissociation energy of 35V. Spectra were collected between m/z of 100 and 500 using XCalibur software (Thermo Fisher). MS$^2$ spectra and predicted fragmentation structures are in the supporting information (FIG. S17-S31 in Appendix A of U.S. Provisional Patent Application No. 62/471,261 and Lin et al. (2017) *Marine Drugs* 15:98) and are also shown in FIG. 4.

Acetylation of Makaluvamines A (1) and J (9)

Three mg samples of 1 and 9 were dissolved in 500 μL of dried pyridine in a 10 mL scintillation tube then 5 μL of acetic anhydride was added and the reaction solution was kept overnight at room temperature. After the solvent was evaporated under nitrogen, the reaction mixture was purified by HPLC (10:90 $CH_3CN:H_2O$ to 60:40 $CH_3CN:H_2O$ with 0.1% formic acid) to yield 13 and 14 from 1, in addition to 15 and 16 from 9. The overall results from these reactions are shown in FIG. 5.

Semi-Synthetic Compound Properties

9-N-acetyl makaluvamine A (13): Red-brown solid; $^1$H NMR (DMSO-$d_6$, 500 MHz) data, see Table 1 and FIG. S13 in Appendix A of U.S. Provisional Patent Application No. 62/471,261 and Lin et al. (2017) *Marine Drugs* 15:98; ESIMS m/z [M+H]$^+$ 244.1122 (calcd for $C_{13}H_{14}N_3O_2$, 244.1081).

9-N-acetyl makaluvamine B (14): Red-brown solid; $^1$H NMR (CD$_3$OD, 600 MHz) data, see Table 1 and FIG. S14 in Appendix A of U.S. Provisional Patent Application No.

62/471,261 and Lin et al. (2017) *Marine Drugs* 15:98; HAESIMS m/z [M+H]+ 242.0927 (calcd for $C_{13}H_{12}N_3O_2$, 242.0924).

15-O-acetyl makaluvamine J (15): Red-brown solid; $^1$H NMR (DMSO-$d_6$, 500 MHz) data, see Table 1 and FIG. S15 in Appendix A of U.S. Provisional Patent Application No. 62/471,261 and Lin et al. (2017) *Marine Drugs* 15:98; HAESIMS m/z M+ 364.1655 (calcd for $C_{21}H_{22}N_3O_3$, 364.1656).

8,15-O-diacetyl-8-hydroxy-5a,7,8a-trien-makaluvamine J (16): Colorless solid; $^1$H NMR (CD$_3$OD, 800 MHz) data, see Table 1 and FIG. S16 in Appendix A of U.S. Provisional Patent Application No. 62/471,261 and Lin et al. (2017) *Marine Drugs* 15:98; HAESIMS m/z [M+H]+ 408.1880 (calcd for $C_{23}H_{26}N_3O_4$, 408.1918).

Cytotoxicity Assays

The soft agar disk diffusion assay, IC$_{50}$ determination, and clonogenic assay were performed as previously described [35].

REFERENCES

1. Thale, Z.; Kinder, F. R.; Bair, K. W.; Bontempo, J.; Czuchta, A. M.; Versace, R. W.; Phillips, P. E.; Sanders, M. L.; Wattanasin, S.; Crews, P. Bengamides revisited: new structures and antitumor studies. *J. Org. Chem.* 2001, 66, 1733-1741.
2. Wenzel, S. C.; Hoffmann, H.; Zhang, J.; Debussche, L.; Haag-Richter, S.; Kurz, M.; Nardi, F.; Lukat, P.; Kochems, I.; Tietgen, H.; Schummer, D.; Nicolas, J.-P.; Calvet, L.; Czepczor, V.; Vrignaud, P.; Mühlenweg, A.; Pelzer, S.; Müller, R.; Brönstrup, M. Production of the bengamide class of marine natural products in myxobacteria: biosynthesis and structure-activity relationships. *Angew. Chem. Int. Ed. Engl.* 2015, 54, 15560-15564.
3. Johnson, T. A.; Sohn, J.; Vaske, Y. M.; White, K. N.; Cohen, T. L.; Vervoort, H. C.; Tenney, K.; Valeriote, F. A.; Bjeldanes, L. F.; Crews, P. Myxobacteria versus sponge-derived alkaloids: The bengamide family identified as potent immune modulating agents by scrutiny of LC-MS/ELSD libraries. *Bioorg. Med. Chem.* 2012, 20, 4348-4355.
4. Furusato, A.; Kato, H.; Nehira, T.; Eguchi, K.; Kawabata, T.; Fujiwara, Y.; Losung, F.; Mangindaan, R. E. P.; De Voogd, N. J.; Takeya, M.; Yokosawa, H.; Tsukamoto, S. Acanthomanzamines A-E with new manzamine frameworks from the marine sponge *Acanthostrongylophora ingens*. *Org. Lett.* 2014, 16, 3888-3891.
5. Waters, A. L.; Peraud, O.; Kasanah, N.; Sims, J. W.; Kothalawala, N.; Anderson, M. A.; Abbas, S. H.; Rao, K. V.; Jupally, V. R.; Kelly, M.; Dass, A.; Hill, R. T.; Hamann, M. T. An analysis of the sponge *Acanthostrongylophora ingens* microbiome yields an actinomycete that produces the natural product manzamine A. *Front. Mar. Sci.* 2014, 1, 1-15.
6. Sakemi, S.; Ichiba, T.; Kohmoto, S.; Saucy, G.; Higa, T. Isolation and structure elucidation of onnamide A, a new bioactive metabolite of a marine sponge, *Theonella* sp. *J. Am. Chem. Soc.* 1988, 110, 4851-4853.
7. Wilson, M. C.; Mori, T.; Rückert, C.; Uria, A. R.; Helf, M. J.; Takada, K.; Gernert, C.; Steffens, U. A. E.; Heycke, N.; Schmitt, S.; Rinke, C.; Helfrich, E. J. N.; Brachmann, A. O.; Gurgui, C.; Wakimoto, T.; Kracht, M.; Crüsemann, M.; Hentschel, U.; Abe, I.; Matsunaga, S.; Kalinowski, J.; Takeyama, H.; Piel, J. An environmental bacterial taxon with a large and distinct metabolic repertoire. *Nature* 2014, 506, 58-62.
8. Radisky, D. C.; Radisky, E. S.; Barrows, L. R.; Copp, B. R.; Kramer, R. A.; Ireland, C. M. Novel cytotoxic topoisomerase II inhibiting pyrroloiminoquinones from Fijian sponges of the genus *Zyzzya*. *J. Am. Chem. Soc.* 1993, 115, 1632-1638.
9. Dijoux, M.-G.; Schnabel, P. C.; Hallock, Y. F.; Boswell, J. L.; Johnson, T. R.; Wilson, J. A.; Ireland, C. M.; van Soest, R.; Boyd, M. R.; Barrows, L. R.; Cardellina, J. H., II Antitumor activity and distribution of pyrroloiminoquinones in the sponge genus *Zyzzya*. *Bioorg. Med. Chem.* 2005, 13, 6035-6044.
10. Ishibashi, M.; Tomoko Iwasaki; Satomi Imai; Shigeru Sakamoto; Kentaro Yamaguchi, A.; Ito, A. Laboratory culture of the Myxomycetes: formation of fruiting bodies of *Didymium bahiense* and its plasmodial production of makaluvamine A. *J. Nat. Prod.* 2001, 64, 108-110.
11. Davis, R. A.; Buchanan, M. S.; Duffy, S.; Avery, V. M.; Charman, S. A.; Charman, W. N.; White, K. L.; Shackleford, D. M.; Edstein, M. D.; Andrews, K. T.; Camp, D.; Quinn, R. J. Antimalarial activity of pyrroloiminoquinones from the Australian marine sponge *Zyzzya* sp. *J. Med. Chem.* 2012, 55, 5851-5858.
12. Schmidt, E. W.; Harper, M. K.; Faulkner, D. J. Makaluvamines H-M and Damirone C from the Pohnpeian sponge *Zyzzya fuliginosa*. *J. Nat. Prod.* 1995, 58, 1861-1867.
13. Perry, N. B.; Blunt, J. W.; McCombs, J. D.; Munro, M. H. G. Discorhabdin C, a highly cytotoxic pigment from a sponge of the genus *Latrunculia*. *J. Org. Chem.* 1986, 51, 5476-5478.
14. Goey, A. K. L.; Chau, C. H.; Sissung, T. M.; Cook, K. M.; Venzon, D. J.; Castro, A.; Ransom, T. R.; Henrich, C. J.; McKee, T. C.; McMahon, J. B.; Grkovic, T.; Cadelis, M. M.; Copp, B. R.; Gustafson, K. R.; Figg, W. D. Screening and biological effects of marine pyrroloiminoquinone alkaloids: potential inhibitors of the HIF-1α/p300 interaction. *J. Nat. Prod.* 2016, 79, 1267-1275.
15. Copp, B. R.; Ireland, C. M.; Barrows, L. R. Wakayin: a novel cytotoxic pyrroloiminoquinone alkaloid from the ascidian *Clavelina* species. *J. Org. Chem.* 1991, 56, 4596-4597.
16. Jordan, P. A.; Moore, B. S. Biosynthetic pathway connects cryptic ribosomally synthesized posttranslationally modified peptide genes with pyrroloquinoline alkaloids. *Cell. Chem. Biol.* 2016, 23, 1-11.
17. Peters, S.; Spiteller, P. Mycenarubins A and B, red pyrroloquinoline alkaloids from the mushroom *Mycena rosea*. *Euro. J. Org. Chem.* 2007, 1571-1576.
18. Peters, S.; Spiteller, P. Sanguinones A and B, blue pyrroloquinoline alkaloids from the fruiting bodies of the mushroom *Mycena sanguinolenta*. *J. Nat. Prod.* 2007, 70, 1274-1277.
19. Hughes, C. C.; MacMillan, J. B.; Gaudêncio, S. P.; Fenical, W.; La Clair, J. J. Ammosamides A and B target myosin. *Angew. Chem. Int. Ed. Engl.* 2009, 48, 728-732.
20. Hughes, C. C.; MacMillan, J. B.; Gaudêncio, S. P.; Jensen, P. R.; Fenical, W. The ammosamides: structures of cell cycle modulators from a marine-derived *Streptomyces* species. *Angew. Chem. Int. Ed. Engl.* 2009, 48, 725-727.
21. Nagata, H.; Yano, H.; Sasaki, K.; Sato, S.; Nakanishi, S.; Takahashi, I.; Tamaoki, T. Inhibition of lymphocyte kinase Lck and phosphatidylinositol 3-kinase by a novel immunosuppressant, lymphostin. *Biosci. Biotechnol. Biochem.* 2002, 66, 501-507.
22. Miyanaga, A.; Janso, J. E.; McDonald, L.; He, M.; Liu, H.; Barbieri, L.; Eustaquio, A. S.; Fielding, E. N.; Carter, G. T.; Jensen, P. R.; Feng, X.; Leighton, M.; Koehn, F. E.; Moore, B. S. Discovery and assembly-line biosynthesis of the lymphostin pyrroloquinoline alkaloid family of mTOR inhibitors in *Salinispora* bacteria. *J. Am. Chem. Soc.* 2011, 133, 13311-13313.

23. Antunes, E. M.; Copp, B. R.; Davies-Coleman, M. T.; Samaai, T. Pyrroloiminoquinone and related metabolites from marine sponges. *Nat. Prod. Rep.* 2005, 22, 62-72.

24. Nag, S.; Nadkarni, D. H.; Qin, J.-J.; Voruganti, S.; Nguyen, T.; Xu, S.; Wang, W.; Velu, S. E.; Zhang, R. Anticancer activity and molecular mechanisms of action of makaluvamines and analogues. *Mol. Cell. Pharmacol.* 2012, 4, 69-81.

25. Zhang, X.; Xu, H.; Zhang, X.; Voruganti, S.; Murugesan, S.; Nadkarni, D. H.; Velu, S. E.; Wang, M.-H.; Wang, W.; Zhang, R. Preclinical evaluation of anticancer efficacy and pharmacological properties of FBA-TPQ, a novel synthetic makaluvamine analog. *Mar. Drugs.* 2012, 10, 1138-1155.

26. Guzmán, E. A.; Johnson, J. D.; Carrier, M. K.; Meyer, C. I.; Pitts, T. P.; Gunasekera, S. P.; Wright, A. E. Selective cytotoxic activity of the marine-derived batzelline compounds against pancreatic cancer cell lines. *Anticancer Drugs* 2009, 20, 149-155.

27. Wang, W.; Nijampatnam, B.; Velu, S. E.; Zhang, R. Discovery and development of synthetic tricyclic pyrroloquinone (TPQ) alkaloid analogs for human cancer therapy. *Front. Chem. Sci. Eng.* 2016, 10, 1-15.

28. Wang, W.; Rayburn, E. R.; Velu, S. E.; Nadkarni, D. H.; Murugesan, S.; Zhang, R. In vitro and In vivo anticancer activity of novel synthetic makaluvamine analogues. *Clin. Cancer Res.* 2009, 15, 3511-3518.

29. Nitiss, J. L. Targeting DNA topoisomerase II in cancer chemotherapy. *Nat. Rev. Cancer* 2009, 9, 338-350.

30. Li, J. N.; Zhu, J. X.; Melvin, W. S.; Bekaii-Saab, T. S.; Chen, C. S.; Muscarella, P. A structurally optimized celecoxib derivative inhibits human pancreatic cancer cell growth. *J. Gastrointest. Surg.* 2006, 10, 207-214.

31. Watts, K. R.; Morinaka, B. I.; Arnagata, T.; Robinson, S. J.; Tenney, K.; Bray, W. M.; Gassner, N. C.; Lokey, R. S.; Media, J.; Valeriote, F. A.; Crews, P. Biostructural features of additional jasplakinolide (Jaspamide) analogues. *J. Nat. Prod.* 2011, 74, 341-351.

32. Subramanian, B.; Nakeff, A.; Tenney, K.; Crews, P.; Gunatilaka, L.; Valeriote, F. A new paradigm for the development of anticancer agents from natural products. *J. Exp. Therapeut. Oncol.* 2006, 5, 195-204.

33. Johnson, T. A.; Tenney, K.; Cichewicz, R. H.; Morinaka, B. I.; White, K. N.; Amagata, T.; Subramanian, B.; Media, J.; Mooberry, S. L.; Valeriote, F. A.; Crews, P. Sponge-derived fijianolide polyketide class: further evaluation of their structural and cytotoxicity properties. *J. Med. Chem.* 2007, 50, 3795-3803.

34. Cichewicz, R. H.; Valeriote, F. A.; Crews, P. Psymberin, a potent sponge-derived cytotoxin from *Psammocinia* distantly related to the pederin family. *Org Lett* 2004, 6, 1951-1954.

35. Valeriote, F. A.; Tenney, K.; Media, J.; Pietraszkiewicz, H.; Edelstein, M.; Johnson, T. A.; Amagata, T.; Crews, P. Discovery and development of anticancer agents from marine sponges: perspectives based on a chemistry-experimental therapeutics collaborative program. *J. Exp. Therapeut. Oncol.* 2012, 10.

36. Johnson, T. A.; Morgan, M. V. C.; Aratow, N. A.; Estee, S. A.; Sashidhara, K. V.; Loveridge, S. T.; Segraves, N. L.; Crews, P. Assessing pressurized liquid extraction for the high-throughput extraction of marine-sponge-derived natural products. *J. Nat. Prod.* 2010, 73, 359-364.

37. McCloud, T. G. High throughput extraction of plant, marine and fungal specimens for preservation of biologically active molecules. *Molecules* 2010, 15, 4526-4563.

38. Chen, T.; Xu, T.; Guo, H.; Liu, Y.; Hu, P.; Yang, X.; Li, X.; Ge, S.; Velu, S. E.; Nadkarni, D. H.; Wang, W.; Zhang, R.; Wang, H. E. Experimental therapy of ovarian cancer with synthetic makaluvamine analog: in vitro and in vivo anticancer activity and molecular mechanisms of action. Plos One 2011, 6, e20729.

Notwithstanding the appended claims, the disclosure is also defined by the following clauses:

1. A compound as set forth in formula (I) or formula (II):

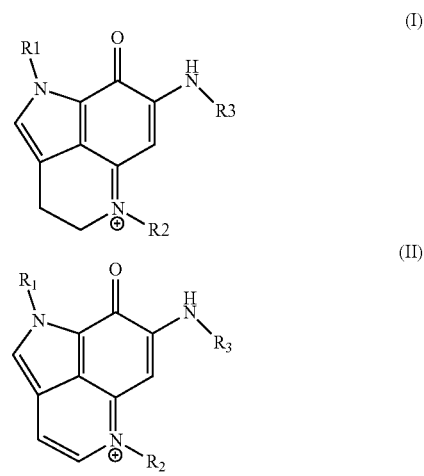

wherein $R^1$ is H, methyl, alkyl, substituted alkyl, alkyl-aryl, or substituted alkyl-aryl;

$R^2$ is methyl, alkyl, substituted alkyl, alkyl-aryl, or substituted alkyl-aryl; and $R^3$ is H, methyl, alkyl, substituted alkyl, alkyl-aryl, or substituted alkyl-aryl.

2. The compound of Clause 1, wherein the compound is that of formula (I).

3. The compound of Clause 1, wherein the compound is that of formula (II).

4. The compound of any one of Clauses 1 to 3, wherein $R^1$ is H.

5. The compound of any one of Clauses 1 to 4, wherein $R^2$ is methyl.

6. The compound of any one of Clauses 1 to 5, wherein $R^3$ is substituted alkyl-aryl.

7. The compound of Clause 6, wherein $R^3$ is

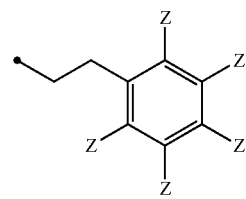

wherein each Z is independently selected from the group consisting of: H, —OH or —OAc, wherein at least one Z is —OH or —OAc.

8. The compound of Clause 7, wherein R³ is

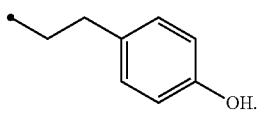

9. The compound of Clause 7, wherein each Z is independently selected from the group consisting of: H or —OAc.
10. The compound of Clause 7, wherein each Z is independently selected from the group consisting of: H or —OAc, wherein R³ comprises at least one —OAc.
11. The compound of Clause 10, wherein R³ is

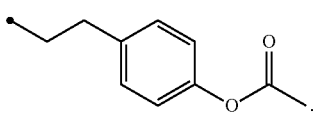

12. The compound of any one of Clauses 1 to 6, wherein R³ is one of:

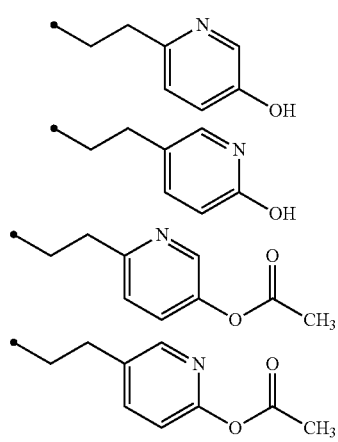

13. A compound as set forth in formula (III):

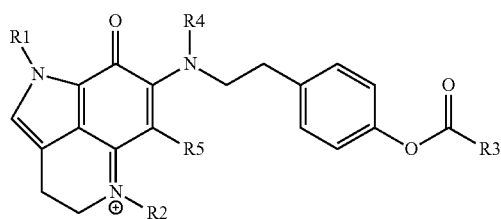

(III)

wherein
R¹ is H, methyl, alkyl, substituted alkyl, alkyl-aryl, or substituted alkyl-aryl;
R² is methyl, alkyl, substituted alkyl, alkyl-aryl, or substituted alkyl-aryl;
R³ is H, methyl, alkyl, substituted alkyl, alkyl-aryl, or substituted alkyl-aryl;
R⁴ is H, methyl, alkyl, substituted alkyl, alkyl-aryl, or substituted alkyl-aryl; and
R⁵ is H, methyl, alkyl, substituted alkyl, alkyl-aryl, or substituted alkyl-aryl.

14. A compound as set forth in formula (IV):

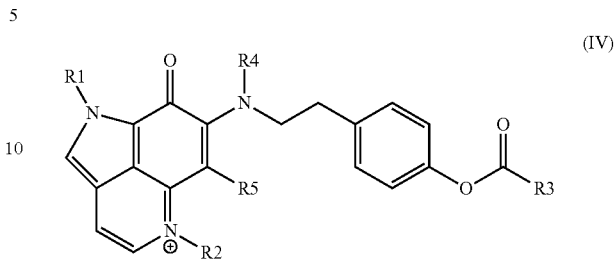

(IV)

wherein
R¹ is H, methyl, alkyl, substituted alkyl, alkyl-aryl, or substituted alkyl-aryl;
R² is methyl, alkyl, substituted alkyl, alkyl-aryl, or substituted alkyl-aryl;
R³ is H, methyl, alkyl, substituted alkyl, alkyl-aryl, or substituted alkyl-aryl;
R⁴ is H, methyl, alkyl, substituted alkyl, alkyl-aryl, or substituted alkyl-aryl; and
R⁵ is H, methyl, alkyl, substituted alkyl, alkyl-aryl, or substituted alkyl-aryl.

15. A compound as set forth in formula (V):

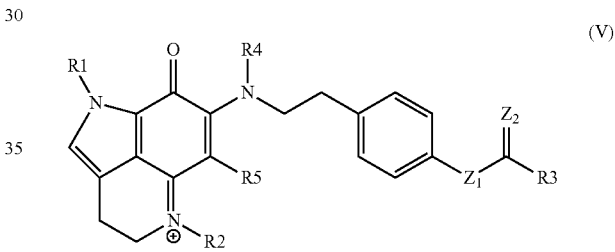

(V)

wherein
R¹ is H, methyl, alkyl, substituted alkyl, alkyl-aryl, or substituted alkyl-aryl;
R² is methyl, alkyl, substituted alkyl, alkyl-aryl, or substituted alkyl-aryl;
R³ is H, methyl, alkyl, substituted alkyl, alkyl-aryl, or substituted alkyl-aryl;
R⁴ is H, methyl, alkyl, substituted alkyl, alkyl-aryl, or substituted alkyl-aryl;
R⁵ is H, methyl, alkyl, substituted alkyl, alkyl-aryl, or substituted alkyl-aryl;
Z¹ is O or N; and
Z² is O or N.

16. A compound as set forth in formula (VI):

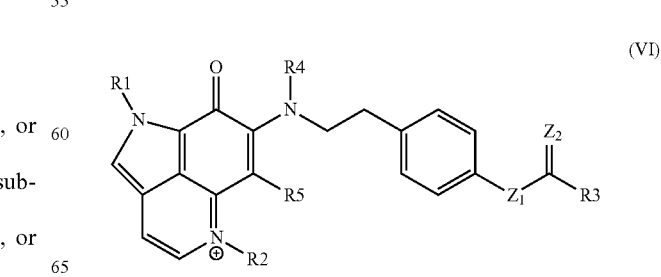

(VI)

wherein

R¹ is H, methyl, alkyl, substituted alkyl, alkyl-aryl, or substituted alkyl-aryl;

R² is methyl, alkyl, substituted alkyl, alkyl-aryl, or substituted alkyl-aryl;

R³ is H, methyl, alkyl, substituted alkyl, alkyl-aryl, or substituted alkyl-aryl;

R⁴ is H, methyl, alkyl, substituted alkyl, alkyl-aryl, or substituted alkyl-aryl;

R⁵ is H, methyl, alkyl, substituted alkyl, alkyl-aryl, or substituted alkyl-aryl;

$Z^1$ is O or N; and $Z^2$ is O or N.

17. A compound as set forth in formula (VII):

(VII)

wherein

R¹ is H, methyl, alkyl, substituted alkyl, alkyl-aryl, or substituted alkyl-aryl; and R² is methyl, alkyl, substituted alkyl, alkyl-aryl, or substituted alkyl-aryl.

18. A compound comprising a pyrrolo[4,3,2-de]quinoline core, wherein the compound comprises one, two, or all three of the following structural motifs: (1) conjugation within the core of the ABC-ring; (2) the presence of a positive charge in the C-ring; and (3) inclusion of a 4-ethyl phenol or 4-ethyl phenol acetate substituent off the B-ring.

19. The compound of Clause 18, comprising each of (1) conjugation within the core of the ABC-ring; (2) the presence of a positive charge in the C-ring; and (3) inclusion of a 4-ethyl phenol or 4-ethyl phenol acetate substituent off the B-ring.

20. A conjugate, comprising:

a targeting moiety; and the compound of any one of Clauses 1 to 19.

21. The conjugate of Clause 20, wherein the targeting moiety specifically binds to a tumor-associated cell surface molecule or a tumor-specific cell surface molecule.

22. The conjugate of Clause 20 or Clause 21, wherein the targeting moiety is an antibody.

23. A pharmaceutical composition, comprising:

the compound of any one of Clauses 1 to 19 or the conjugate of any one of Clauses 20 to 22; and a pharmaceutically acceptable carrier.

24. The pharmaceutical composition of Clause 23, wherein the composition is formulated for parenteral administration.

25. A method, comprising:

administering to an individual in need thereof a therapeutically effective amount of a compound of any one of Clauses 1 to 19, a conjugate of any one of Clauses 20 to 22, or a pharmaceutical composition of Clause 23 or Clause 24.

26. The method according to Clause 25, wherein the individual in need thereof has a cell proliferative disorder, and the administering is effective in treating the cell proliferative disorder.

27. The method according to Clause 26, wherein the cell proliferative disorder is cancer.

28. The method according to Clause 27, wherein the cancer is pancreatic cancer.

29. The method according to Clause 27, wherein the cancer is ovarian cancer.

30. A kit, comprising:

a therapeutically effective amount of a compound of any one of Clauses 1 to 19, a conjugate of any one of Clauses 20 to 22, or a pharmaceutical composition of Clause 23 or Clause 24.

31. The kit of Clause 30, wherein the kit comprises the pharmaceutical composition of Clause 23 or Clause 24.

32. The kit of Clause 31, wherein the pharmaceutical composition is present in one or more unit dosages.

33. The kit of Clause 32, wherein the kit comprises the composition in two or more unit dosages.

34. The kit of any one of Clauses 30 to 33, comprising instructions to treat an individual in need thereof by administering the compound, conjugate, or pharmaceutical composition to the individual.

35. The kit of any one of Clauses 30 to 34, comprising instructions to treat an individual having a cell proliferative disorder by administering the compound, conjugate, or pharmaceutical composition to the individual.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A compound selected from the group consisting of:

-continued
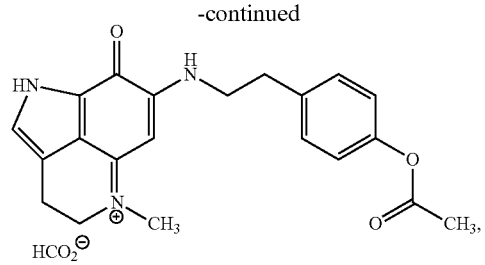
and
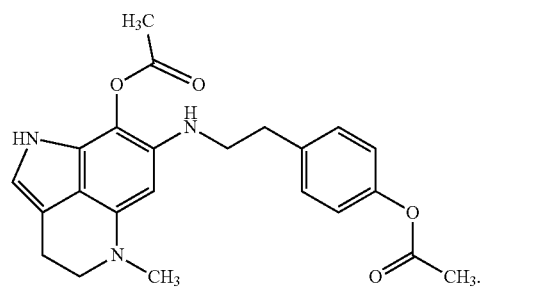
2. A pharmaceutical composition, comprising:
the compound of claim 1; and
a pharmaceutically acceptable carrier.
* * * * *